(12) United States Patent
Donini et al.

(10) Patent No.: US 8,124,721 B2
(45) Date of Patent: *Feb. 28, 2012

(54) PEPTIDES FOR MODULATING INNATE IMMUNITY

(75) Inventors: Oreola Donini, Coquitlam (CA); Annett Rozek, Port Moody (CA); Shannon Wayne Lentz, Vancouver (CA)

(73) Assignee: INIMEX Pharmaceuticals Inc., Burnaby, BC (CA)

( * ) Notice: Subject to any disclaimer, the term of this patent is extended or adjusted under 35 U.S.C. 154(b) by 546 days.

This patent is subject to a terminal disclaimer.

(21) Appl. No.: 12/083,086

(22) PCT Filed: Oct. 4, 2006

(86) PCT No.: PCT/CA2006/001650
§ 371 (c)(1),
(2), (4) Date: Apr. 4, 2008

(87) PCT Pub. No.: WO2007/038876
PCT Pub. Date: Apr. 12, 2007

(65) Prior Publication Data
US 2009/0246217 A1 Oct. 1, 2009

Related U.S. Application Data

(60) Provisional application No. 60/722,962, filed on Oct. 4, 2005, provisional application No. 60/722,958, filed on Oct. 4, 2005, provisional application No. 60/722,959, filed on Oct. 4, 2005.

(51) Int. Cl.
C07K 14/00 (2006.01)
A61K 39/00 (2006.01)

(52) U.S. Cl. ................... 530/300; 424/184.1

(58) Field of Classification Search ............ None
See application file for complete search history.

(56) References Cited

U.S. PATENT DOCUMENTS

| 2003/0119750 A1 | 6/2003 | Demuth et al. |
| 2003/0130199 A1 | 7/2003 | Von Hoersten et al. |
| 2003/0176357 A1 | 9/2003 | Pospisilik et al. |
| 2004/0235049 A1 | 11/2004 | Melnyk et al. |
| 2005/0069911 A1 | 3/2005 | Lee |
| 2005/0191296 A1 | 9/2005 | Kaempfer et al. |
| 2008/0118525 A1 | 5/2008 | Donini |
| 2009/0062512 A1 | 3/2009 | Hildebrand |
| 2009/0186824 A1 | 7/2009 | Donini |

FOREIGN PATENT DOCUMENTS

| EP | 0 045 665 | 2/1982 |
| WO | WO 01/31019 | 5/2001 |
| WO | WO03/002596 | 1/2003 |
| WO | WO03/048383 | 6/2003 |
| WO | WO 03/063759 | 8/2003 |
| WO | WO 03/106491 | 12/2003 |
| WO | WO 2004/031211 | 4/2004 |
| WO | WO 2005/025607 | 3/2005 |
| WO | WO 2005/026204 | 3/2005 |
| WO | WO2005/081628 A2 | 9/2005 |
| WO | WO 2006/005190 | 1/2006 |
| WO | WO 2006/015886 | 2/2006 |
| WO | WO 2006/038208 | 4/2006 |
| WO | WO 2006/050611 | 5/2006 |
| WO | WO 2006/114478 | 11/2006 |
| WO | WO 2008/040111 | 4/2008 |

OTHER PUBLICATIONS

Christopherson, et al. "Cell Surface Peptidase CD26/Dipeptidylpeptidase IV Regulates CXCL12/Stromal Cell-Derived Factor-1α-Mediated Chemotaxis of Human Cord Blood CD34+ Progenitor Cells" (The Journal of Immunology, 2002, 169: 7000-7008).*
Iwata S. et al. "CD26/dipeptidyl peptidase IV differentially regulates the chemotaxis of T cells and monocytes toward RANTES: possible mechanism for the switch from innate to acquired immune response" International Immunology, vol. 11, No. 3, pp. 417-426, 1999.*
Lambeir et al. "Kinetic Investigation of Chemokine Truncation by CD26/Dipeptidyl Peptidase IV Reveals a Striking Selectivity within the Chemokine Family" The Journal of Biological Chemistry 276(32):29839-29845, 2001.*
Shoukry Naglaa H et al: "Conserved hierarchy . . . infections." Journal of Immunology, vol. 172, No. 1, Jan. 1, 2004, pp. 483-492, XP002592693 ISSN: 0022-176.
Wrenger Sabine et al: "The N-terminal X-X-Pro sequence of the HIV-1 Tat protein . . . T cells" FEBS Letters, vol. 383, No. 3, 1996, pp. 145-149, XP002531562; ISSN: 0014-5793.
Augustyns K et al: "The . . . " Current Medicinal Chemistry Bentham Science Publishers BV BE, vol. 12, No. 8, Jan. 1, 2005 pp. 971-998 XP009066443; ISSN 0929-8673.
Wrenger Sabine et al: "The N-terminal . . . " Journal of Biological Chemistry, vol. 272, No. 48, Nov. 28, 1997, pp. 30283-30288, XP002531563 ISSN: 0021-9258.
Blazquez M V, et al. "Selective decrease of CD26 expression in T cells from HIV-1-infected individuals." J. Immunol. Nov. 1, 1992; 149(9):3073-7.
Vanham G, et al. "Decreased expression of the memory marker CD26 on both CD4+ and CD8+ T lymphocytes of . . . " J Acquir Immune Defic Syndr. Jul. 1993; 6(7): 749-57.
Oravecz T, et al. "CD26 expression correlates with entry, replication . . . " Nat Med Sep. 1995; 1(9):919-26 Comment in: Nat. Med. Sep. 1995; 1(9):881-2.
Nishikawa Y, et al. [Adenosine deaminase isoenzymes in patients with Graves' disease] Rinsho Byori. Oct. 1995,43(10):1057-60. [Article in Japanese].

(Continued)

*Primary Examiner* — Bo Peng
(74) *Attorney, Agent, or Firm* — Howson & Howson LLP

(57) ABSTRACT

In one aspect, the present invention provides isolated novel peptides that can be used to modulate innate immunity in a subject, and/or for the treatment of an immune-related disorder, including treating and preventing infection by modulating innate immunity. Also provided are an agent reactive with this peptide, a pharmaceutical composition that includes the peptide, an isolated nucleic acid molecule encoding the peptide, a recombinant nucleic acid construct that includes the nucleic acid molecule, at least one host cell comprising the recombinant nucleic acid construct, and a method of producing the peptide using the host cell. The present invention further provides a method for treating and/or preventing infection in a subject by administering the peptide of the invention to the subject, thereby modulating innate immunity in the subject. Additionally, the present invention provides a method for predicting whether a subject would be responsive to treatment with a peptide of the invention.

4 Claims, 11 Drawing Sheets

OTHER PUBLICATIONS

Eguchi K, et al. "Increment in the Ta1+ cells in the peripheral blood and thyroid tissue of patients with Graves' disease." J Immunol Jun. 15, 1989; 142(12):4233-40.
Stecca B A, et al. "Aberrant dipeptidyl peptidase IV (DPP IV/CD26) expression in human hepatocellular carcinoma." J Hepatol. Aug. 1997; 27(2):337-45.
Nakao H, et al. "Increment of Ta1 positive cells in peripheral blood from patients with rheumatoid arthritis." J Rheumatol. Jul. 1989; 16(7):904-10.
Constantinescu C S, et al. "A longitudinal study of the T cell activation marker CD26 in chronic progressive multiple sclerosis." J Neurol Sci. Jun. 1995; 130(2):178-82.
Morimoto C, Schlossman S F. The structure and function of CD26 in the the T-cell immune response. Immunol. Review. 1998, 161: 55-70.
Evans BE, et al. "Design of nonpeptidal ligands for a peptide receptor: cholecystokinin antagonist." J Med Chem. Jul. 1987;30(7):1229-1239.
Morley, "Modulation of the Action of Regulatory Peptides by Structural Modification", (General Review) Trends Pharm. Sci. pp. 463-468 (1980).
Schols D, et al. "CD26-processed RANTES (3-68), but not intact RANTES, . . . " Antiviral Res. Oct. 1998; 39(3):175-87. Erratum in: Antiviral Res Jan. 1999; 40(3):189-90.
Durinx C et al., (2001) Reference values for plasma dipeptidyl-peptidase IV activity and their association with other laboratory parameters. Clin Chem Lab Med. 39(2):155-9.
Tanaka, S., et al., Anti-arthritic effects of the novel dipeptidyl peptidase IV inhibitors TMC-2A and TSL-225. Immunopharmacology 1998, 40: 21-26.
Tanaka, S., et al.,: Suppression of arthritis by the inhibitors of dipeptidyl peptidase IV. Int J. Immunopharmacol 1997, 19:15-24.
STN Search Results, Apr. 15, 2011 (33 pages).
STN Search Results, Apr. 15, 2011 (4 pages).
STN Search Results, Mar. 24, 2011 (146 pages).
STN Search Results, Mar. 24, 2011 (43 pages).
Tanabe, H. et al, "Paneth Cell Alpha-Defensins From Rhesus Macaque Small Intestine", Infection and Immunity, Mar. 2004, vol. 72, No. 3, pp. 1470-1478, ISSN 0019-9567.
Lau, Y. E. et al, "Interaction and Cellular Localization of the Human Host Defence . . . ", Infection and Immunity, Jan. 2005, vol. 73, No. 1, pp. 583-591, ISSN 0019-9567.
Boris Weinstein, "Chemistry and Biochemistry of Amino Acids, Peptides, and Proteins" (Marcel Dekker, Inc., New York, 1983), pp. 267-357.
Kelsen et al., "The Chemokine Receptor CXCR3 and Its Splice Variant are Expressed in Human Airway Epithelial Cells", Am. J. Physiol. Lung Cell Mol. Physiol 287: L584, 2004.
Oravecz et al., "Regulation of the Receptor Specificity and Function of the Chemokine RANTES by Dipeptidyl Peptibase IV (CD26)-Mediated Cleavage", J Exp Med 186: 1865, 1997.
Iwata et al., "CD26/Dipeptidyl Peptibase IV Differentially Regulates the Chemotaxis of T Cells and Monocytes Toward RANTES . . . ", Int. Immunol. 11: 417-426, 1999.
Hinke et al., "Dipeptidyl Peptibase IV (DPIV/CD26) Degradation of Glucagon", J. Biol. Chem. 275(6): 3827-3834, 2000.
Marguet et al., "Enhanced Insulin Secretion and Improved Glucose Tolerance in Mice Lacking CD26", PNAS 97(12): 6874-6879, 2000.
Fotouhi et al, Potent peptide inhibitors of stromelysin based on the prodomain region of matrix metalloproteinases, Journal of Biological Chemistry, 269(48):30227-31 (Dec. 1994).
Ng et al, Predicting deleterious amino acid substitutions, Genome Research, 11(5):863-74 (May 2001).
Bowie et al, Deciphering the message in protein sequences: tolerance to amino acid substitutions, Science, 247(4948):1306-10 (Mar. 1990).
Lazar et al, Transforming growth factor alpha: mutation of aspartic acid 47 and leucine 48 results in different biological activities, Molecular and Cellular Biology, 8(3):1247-52 (Mar. 1988).
Burgess et al, Possible dissociation of the heparin-binding and mitogenic activities of heparin-binding (acidic fibroblast) growth factor-1 from its receptor-binding activities by site-directed mutagenesis of a single lysine residue, Journal of Cell Biology, 111:2129-38 (Nov. 1990).
Houghten et al, New approaches to Immunization, Vaccines 86, Cold Spring Harbor Laboratory, p. 21-25, 1986.
Colman, Effects of amino acid sequence changes on antibody-antigen interactions, Research in Immunology, 145:33-36 (Jan. 1994).
Yamamoto et al, Biogenic peptides and their potential use, Current Pharmaceutical Design, 9(16):1345-55 (2003).
Katoh et al, Discrimination between α-amylase isozymes with anti-peptide antibodies, Chemical Engineering Journal, 65(2):105-8 (May 1997).
Nomura et al, Purification of angiotensin I-converting enzyme inhibitors in pelagic thresher *Alopias pelagicus* muscle hydrolysate and viscera extracts, Fisheries Science, 68(4):954-6 (2002).
Tam JP, Synthetic peptide vaccine design: synthesis and properties of a high-density multiple antigenic peptide system, Proceedings of the National Academy of Sciences USA, 85(15):5409-13 (Aug. 1988).
Communication dated Jun. 26, 2009 including Extended European Search Report issued in related EP patent application No. 06790808.7.
Communication dated Jul. 6, 2010 issued in corresponding European patent application No. 07719467.8.
Communication dated Jun. 18, 2010 including Extended European Search Report issued in corresponding EP patent application No. 07719467.8.
Applicants' response dated Jan. 6, 2011 to Communication dated Jul. 6, 2010 in corresponding EP patent application No. 07719467.8.
International Preliminary Report on Patentability dated Apr. 7, 2009 issued in related international patent application No. PCT/CA2007/000537.
International Search Report dated Jul. 20, 2007 issued in related international patent application No. PCT/CA2007/000537.
Communication dated Nov. 29, 2010 including Extended European Search Report issued in related EP patent application No. 10003191.3.
Communication dated Aug. 4, 2010 including partial European Search Report issued in related EP patent application No. 10003191.3.
Office Action dated Dec. 17, 2008 issued in related U.S. Appl. No. 11/730,695.
Paton et al, Phylogeny and evolution of basils and allies (Ocimeae, Labiatae) based on three plastid DNA regions, Molecular phylogenetics and Evolution, 31:277-299 (Apr. 2004).
Genbank Accession No. CAD45512, accessed Nov. 14, 2011.
Kasprzykowski et al, Peptidyl Diazomethylketones as Cysteine Protease Inhibitors Structurally based Upon the Inhibitory Centers of Cystatins, Polish J. Chem, 75:831-837 (Feb. 2001).
Office Action dated Sep. 15, 2011 issued in corresponding Israeli patent application No. 190601.

\* cited by examiner

PEPTIDES FOR MODULATING INNATE IMMUNITY

PRIOR RELATED APPLICATIONS

This application is a national phase entry of PCT/CA2006/001650 filed Oct. 4, 2006 designating the United States, which claims priority from United States Provisional Patent Applications, 60/722,962; 60/722,958; and 60/722,959, filed Oct. 4, 2005, all entitled "NOVEL PEPTIDES FOR TREATING AND PREVENTING INFECTION BY MODULATING INNATE IMMUNITY", and which are, all incorporated herein by reference. International Patent Application No. PCT/CA2006/001650 was published in English under Article 21 of the Patent Cooperation Treaty under WO 2007/038876 on Apr. 12, 2007.

FIELD OF THE INVENTION

This invention relates to peptides for use in treating and preventing immune-related disorders, including treating and preventing infection by modulating innate immunity. In one aspect, the invention relates to compositions and uses thereof for modulating innate immunity. In another aspect, the invention provides novel peptides and uses thereof effective in reducing DPPIV activity.

BACKGROUND OF THE INVENTION

A variety of microorganisms, including viruses, bacteria, fungi, and parasites, can cause disease. Microbial cells are distinct from the cells of animals and plants—which are unable to live alone in nature, existing only as parts of multicellular organisms. Microbial cells can be pathogenic or non-pathogenic, depending, in part, on the microorganism and the status of the host. For example, in an immunocompromised host, a normally harmless bacterium can become a pathogen. Entry into host cells is critical for the survival of bacterial pathogens that replicate in an intracellular milieu. For organisms that replicate at extracellular sites, the significance of bacterial entry into host cells is less well defined.

Drug resistance remains an obstacle in the ongoing effort to fight infection. For example, penicillin was effective in treating *Staphylococcus aureus*, until the bacterium became resistant. Throughout the second half of the 20$^{th}$ century, new antibiotics, such as vancomycin and methicillin, were developed; these successfully cured *S. aureus* infections. However, methicillin-resistant strains of *S. aureus* evolved in the 1970s, and have been plaguing hospitals worldwide ever since. More recently, vancomycin-resistant strains of *S. aureus* have surfaced.

With the increasing threat of resistance to antimicrobial drugs and the emergence of new infectious diseases, there exists a continuing need for novel therapeutic compounds. Therapeutics that act on the host, not the pathogen, are desirable, because they do not encourage pathogenic resistance. In particular, drugs that act on the host via the innate immune system provide a promising source of therapeutics.

Host defense against microorganisms begins with the epithelial barriers of the body and the innate immune system, and culminates in the induction of the adaptive immune response. The host innate immune response encompasses a set of highly-conserved mechanisms that recognize and counter microbial infections. Elements of innate immunity are continuously maintained at low levels, and are activated very rapidly when stimulated. The innate immune response begins with events that occur immediately after exposure to a microbial pathogen. Events associated with adaptive immunity, such as rearrangement of immunoglobulin receptor genes, are not considered part of the innate response.

There is evidence to indicate that innate responses are instrumental in controlling most infections, and also contribute to inflammatory responses. Inflammatory responses triggered by infection are known to be central components of disease pathogenesis. The importance of Toll-like receptors (TLRs) in the innate immune response has also been well characterized. The mammalian family of TLRs recognizes conserved molecules, many of which are found on the surfaces of, or are released by, microbial pathogens. There are numerous other mechanisms, less well characterized, that initiate and/or contribute to the host innate defense.

The innate immune system provides a range of protective mechanisms, including epithelial-barrier function and secretion of cytokines and chemokines. To date, four families of chemokines have been categorized, according to the number of conserved N-terminal cysteine motifs: C, CC, CXC, and CX3C, where X is a non-conserved amino acid residue. The CXC chemokines are known to be chemotactic for cells bearing the CXCR3 receptor, including monocytes, activated T cells (Th1), and NK cells. Primary human airway epithelial cells, and the cell line 16-HBE, constitutively express the CXCR3 receptor and its ligands, IP-10, I-TAC, and MIG (Kelsen et al., The chemokine receptor CXCR3 and its splice variant are expressed in human airway epithelial cells, *Am. J. Physiol. Lung Cell Mol. Physiol.*, 287:L584, 2004). Furthermore, CXCR3 ligands induce chemotactic responses and actin reorganization in 16-HBE cells (Kelsen et al., The chemokine receptor CXCR3 and its splice variant are expressed in human airway epithelial cells, *Am. J. Physiol. Lung Cell Mol. Physiol.*, 287:L584, 2004).

Further, the type II transmembrane serine protease dipeptidyl peptidase IV (DPPIV), also known as CD26 or adenosine deaminase binding protein, is a major regulator of various physiological processes including immune functions. CD26/DPPIV is a 110-kD cell surface glycoprotein that is mainly expressed on mature thymocytes, activated T-cells, B-cells, NK-cells, macrophages, and epithelial cells. It has at least two functions, a signal transduction function and a proteolytic function (Morimoto C, Schlossman S F. The structure and function of CD26 in the T-cell immune response. Immunol. Review. 1998, 161: 55-70). One of its cellular roles involves modulation of chemokine activity by cleaving dipeptides from the chemokine N-terminus. The modulation of the NH$_2$ termini of chemokines is of great importance not only for binding to their receptors and the following reactions but also for altering the receptor specificity of the processed chemokine. DPPIV activity has been associated with a number of immune-related conditions.

SUMMARY OF THE INVENTION

The inventors have discovered that peptides having the amino acid sequence of one of the peptides listed and described in TABLE 1 or an analogue, derivative, or variant thereof can enhance a host's innate immunity. In one aspect, the immunomodulatory peptides of the invention were found to lack antimicrobial activity while demonstrating an ability to improve survival in infected hosts. In another aspect, the invention provides peptides that modulate DPPIV activity. In one aspect the invention provides peptides that reduce DPPIV activity. In yet another aspect, the invention provides peptides which can be used in the diagnosis, treatment or prevention of an immunological disorder, such as one associated with DPPIV activity and/or innate immunity.

Accordingly, in one aspect, the present invention provides an isolated peptide that includes the amino acid sequence of any one of TABLE 1 or an analogue, derivative, or variant thereof or obvious chemical equivalent thereof or a peptide comprising said peptide. In one embodiment the peptide is up to 10 amino acids comprising said peptide. By way of example, the isolated peptide may have a modified C-terminus (e.g., an amidated C-terminus) and/or a modified N-terminus. The isolated peptide of the invention may further include the amino acid sequence of TABLE 1 as modified by at least one substitution of a D amino acid. The isolated peptide may further include a modified backbone, by way of example, wherein the N-terminus is modified from an amide to an N-methyl. In one aspect, those modified peptides which retain the immunological activity of the parent peptide and obvious chemical equivalent thereto which retain said activity are encompassed within the scope of the present invention.

In another aspect, the present invention further provides an agent reactive with an isolated peptide that includes the amino acid sequence of TABLE 1 or an analogue, derivative, or variant thereof. In one embodiment, the agent is a non-naturally occurring antibody (e.g., a polyclonal or monoclonal antibody). In one embodiment, the antibody is made using a MAPS Antigen attached to the peptide of the present invention via 2 glycine residues inserted at the C-terminus of the peptide. The construct can then be administered to an animal, such as a rabbit and the antibody harvested using procedures well known in the art. In one aspect, such agents can be labeled or used to label peptides of the invention. In another aspect such agents can be used in diagnostic and screening methods to monitor agents that may modulate peptide activity or to quantitate the amount of the peptide.

In yet another aspect, the present invention provides an isolated nucleic acid molecule encoding an isolated peptide having or comprising the amino acid sequence of TABLE 1 or an analogue, derivative, or variant thereof. Also provided is a recombinant nucleic acid construct that includes the nucleic acid molecule operably linked to an expression vector.

In a further aspect, the present invention provides at least one host cell comprising the recombinant nucleic acid construct of the invention. Also provided is a method for producing a peptide having or comprising the amino acid sequence of TABLE 1 or an analogue, derivative, or variant thereof, by: (a) culturing the at least one host cell, under conditions allowing expression of the peptide; and (b) recovering the peptide from the at least one host cell or culture medium thereof.

In still another aspect, the present invention provides a pharmaceutical composition that includes an isolated peptide having or comprising the amino acid sequence of TABLE 1 or an analogue, derivative, or variant thereof (including a pharmaceutically-acceptable salt, addition salt, or ester of any of the foregoing or polymorph), in combination with a pharmaceutically-acceptable carrier, diluent, or excipient.

In another aspect, the present invention provides a method for treating and/or preventing infection (e.g., a microbial infection) in a subject, by administering to the subject a peptide having or comprising the amino acid sequence of TABLE 1 or an analogue, derivative, or variant thereof or obvious chemical equivalent thereof. By way of example, the subject may have, or be at risk of having, infection. In one embodiment, the peptide modulates innate immunity in the subject, thereby treating and/or preventing the infection in the subject. The present invention further provides a method for identifying a microbial infection that can be treated with a peptide of the invention. In another aspect, the invention provides a method for treating or preventing a DPPIV-related condition or disorder.

Exemplary infections which may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant *enterococcus*). In another embodiment, the infection is a fungal infection (e.g., infection by a mould, a yeast, or a higher fungus). In still another embodiment, the infection is a parasitic infection (e.g., infection by a single-celled or multicellular parasite, including *Giardia duodenalis, Cryptosporidium parvum, Cyclospora cayetanensis*, and *Toxoplasma gondii*). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus)).

In accordance with the method of the present invention, a peptide having or comprising the amino acid sequence of TABLE 1 or an analogue, derivative, or variant thereof may be administered to the subject directly (i.e., by administering the peptide itself) or indirectly (e.g., by administering to the subject a nucleic acid sequence encoding the peptide, in a manner permitting expression of the peptide in the subject). The peptide of the invention (or nucleic acid encoding same) may be administered to the subject orally, parenterally (e.g., intradermally, intramuscularly, intraperitoneally, intravenously, or subcutaneously), transdermally, intranasally, by pulmonary administration (e.g., by intratracheal administration), and/or by osmotic pump.

In yet another aspect, the present invention provides a method for predicting whether a subject would be responsive to treatment with a peptide comprising the amino acid sequence of TABLE 1 or an analogue, derivative, or variant thereof, by assaying a diagnostic sample of the subject for DPPIV activity, wherein modulation, such as reduction of DPPIV activity is indicative that the subject would be responsive to treatment by the peptide. In one aspect, the subject has or is suspected of having a DPPIV-related condition or disorder.

Additional aspects and advantages of the present invention will be apparent in view of the description which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The invention will now be described in relation to the drawings, in which.

DETAILED DESCRIPTION OF THE INVENTION

Definitions

Figure 1A:
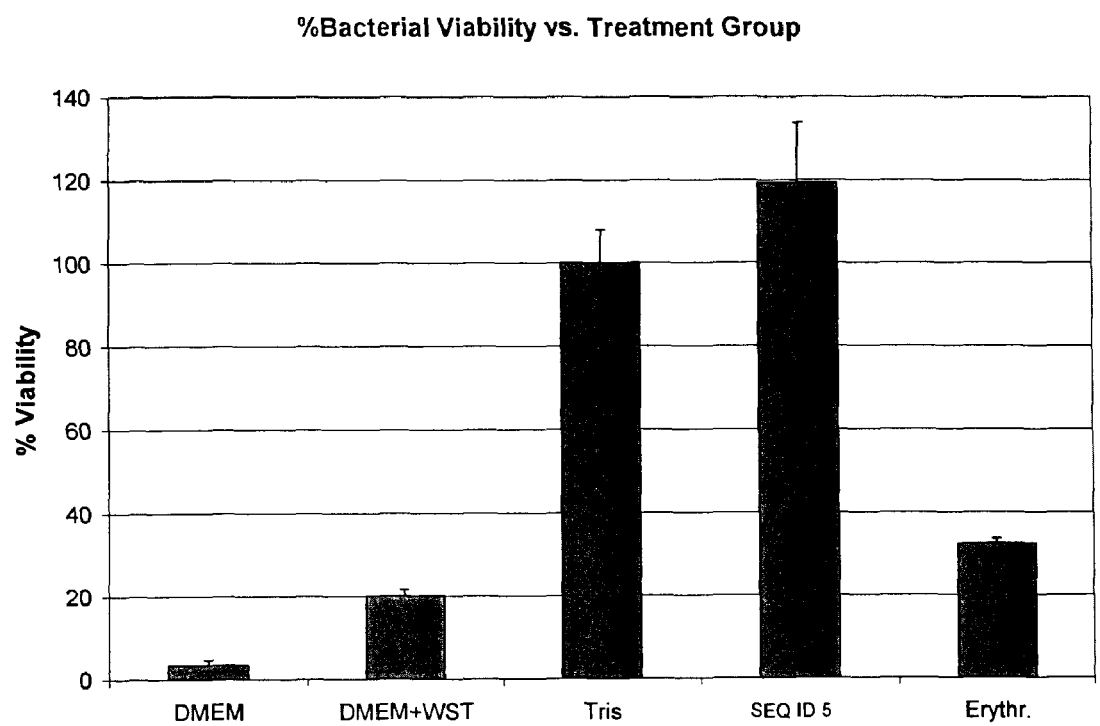
FIGS. 1A and B depicts the results of the experiment described in Example 2. % Viability=the amount of bacterial growth relative to the vehicle control (Tris), which is set to 100% bacterial survival with respective peptides SEQ ID NOs: 5 and 47; Erythr.=erythromycin.

"DPPIV-related disorder" or "DPPIV-related condition" or "DPPIV associated condition" as used herein means any medical condition that has been correlated with DPPIV activity and wherein modulation of said activity can be used to treat and/or prevent or diagnose said condition. Examples of such conditions include, but are not limited to: HIV/AIDS, autoimmune conditions, such as Rheumatoid Arthritis, multiple sclerosis, cancer (e.g. colon and lung), diabetes, and Graves disease.

"Immune-related disorder" is a condition that is associated with the immune system of a subject, either through activation or inhibition of the immune system, or that can be treated, prevented or diagnosed by targeting a certain component of the immune response in a subject, such as the innate immune response.

"Immunologically active" as used herein refers to innate immune activity (e.g. the ability to modulate the innate immune response or component thereof in a subject) or the ability to modulate DPPIV activity.

"Modulate" or "Modulating" as used herein, for instance such as modulating DPPIV activity or a particular response, encompasses the increase or decrease of activity or response in relation to a control or the normal or baseline level of activity or response under certain conditions. It can also encompass the maintaining of a level of activity or response under conditions that would normally increase or decrease the level of activity of the peptide or response.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, trifluoroacetate and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as trifluoroacetic acid, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs, see Bundgaard, H., ed., (1985) Design of Prodrugs, Elsevier Science Publishers, Amsterdam.

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., supra. These esters are typically formed from the corresponding carboxylic acid and an alcohol. Generally, ester formation can be accomplished via conventional synthetic techniques. (See, e.g., March, Advanced Organic Chemistry, 3rd Ed., John Wiley & Sons, New York (1985) p. 1157 and references cited therein, and Mark et al., Encyclopedia of Chemical Technology, John Wiley & Sons, New York (1980).) The alcohol component of the ester will generally comprise (i) a $C_{-2}$—$C_{-12}$ aliphatic alcohol that can or can not contain one or more double bonds and can or can not contain branched carbon chains or (ii) a $C_{-7}$—$C_{-12}$ aromatic or heteroaromatic alcohols. This invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H., ed., supra. These amides are typically formed from the corresponding carboxylic acid and an amine. Generally, amide formation can be accomplished via conventional synthetic techniques. (See, e.g., March, Advanced Organic Chemistry, 3rd Ed., John Wiley & Sons, New York (1985) p. 1152 and Mark et al., Encyclopedia of Chemical Technology, John Wiley & Sons, New York (1980).) This invention also contemplates the use of those compositions which are both amides as described herein and at the same time are the pharmaceutically acceptable acid addition salts thereof.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All immunologically active stereoisomers are included within the scope of the invention.

"Therapeutically or pharmaceutically effective amount" as applied to the compositions of the instant invention refers to the amount of composition sufficient to induce a desired biological result. That result can be alleviation of the signs, symptoms, or causes of a disease, or any other desired alteration of a biological system. For instance, in the present invention, the result will typically involve enhancement of the innate immune response, reduction of DPPIV activity and/or modulation (such as inhibition or reduction or non-stimulation) of the inflammatory responses to infection or tissue injury.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. In addition, the abbreviation NaI is used to denote 1-naphthylalanine; Ornithine is Orn or O, Cit is citrulline Hci is citrulline with one more methylene groups, and Vx or Valine x, wherein the "x" refers to a variation in the backbone of the amino acid, wherein the amino acid linkage is no longer an amide bond, but a methylated amine, this similarly applies to other amino acids with the "x" designation. Also, 2,4-diaminobutyric acid is Dab; 2,3-diaminopropionic acid is Dpr or Dapa; N-(4-aminobutyl)-glycine is Nlys; hSer is homoserine; Hyp is hydroxyproline; Val(betaOH) is hydroxyvaline; D-Pro is 3,4-dehydroproline; Pyr is pyroglutamine (proline with C=O in ring); Proline with fluorine substitutions on the ring; 1,3-thiazolidine-4-carboxylic acid (proline with S in ring); Thi is beta-(2-thienyl)-alanine; Abu is 2-aminobutyric acid; Nva is norvaline; Nle is norleucine; Hol is homoleucine; and Aib is alpha-aminoisobutyric acid.

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J., Adv. Drug Res. 15:29 (1986); Veber and Freidinger, TINS p. 392 (1985); and Evans et al., J. Med. Chem. 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm peptide (i.e., a peptide that has a biological or pharmacological activity), such as naturally-occurring receptor-binding peptide, but have one or more peptide linkages optionally replaced by a linkage selected from the group consisting of: —CH$_2$NH—, —CH$_2$.S—, —CH$_2$=CH$_2$—, —CH=CH— (cis and trans), —COCH$_2$—, —CH(OH)CH$_2$—, and —CH$_2$SO—, by methods known in the art and further described in the following references: Spatola, A. F. in Chemistry and Biochemistry of Amino Acids, Peptides and Proteins, B. Weinstein, eds., Marcel Dekker, New York, p. 267 (1983); Spatola, A. F., Vega Data (March 1983), Vol. 1, Issue 3, PEPTIDE BACKBONE MODIFICATIONS (general review); Morley, Trends Pharm Sci (1980) pp. 463 468 (general review); Hudson, D. et al., Int J Pept Prot Res 14:177 185 (1979): (—CH$_2$NH—, CH$_2$CH$_2$—); Spatola et al., Life Sci 38:1243 1249 (1986): (—CH$_2$—S); Hann J. Chem. Soc. Perkin Trans. I 307 314 (1982): (—CH—CH—, cis and trans); Almquist et al., J Med Chem 23:1392 1398 (1980): (—COCH$_2$—); Jennings-White et al., Tetrahedron Lett 23:2533 (1982): (—COCH$_2$—); Szelke et al., European Application. EP 45665 CA: 97:39405 (1982) (—CH(OH)CH$_2$.); Holladay et al., Tetrahedron Lett 24:4401 4404 (1983): (—C(OH)CH$_2$—); and Hruby Life Sci 31:189 199 (1982): (—CH$_2$—S—); each of which is incorporated herein by reference. In one aspect, the non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivatization (e.g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (e.g., D-lysine in place of L-lysine) may be used to generate more stable peptides. It is appreciated that those D-amino acid substitutions wherein immunological activity of the peptide is retained are desired.

Description

As described herein, the inventors have identified novel peptides having and/or comprising the amino acid sequence as shown in TABLE 1 or an analogue, derivative, or variant of the amino acid sequences disclosed therein. The inventors have also demonstrated that a peptide having or comprising one of the amino acid sequences of TABLE 1 and an amidated C-terminus has therapeutic utility in the enhancement of innate immunity. In particular, the inventors have shown that a peptide comprising an amino acid sequence of TABLE 1 lacked antimicrobial efficacy against S. aureus, yet provided in vivo protection in mice infected with S. aureus. The peptide enhanced the host response to infection, resulting in improved bacterial clearance and host survival. Thus, the novel peptides described can be used as a therapeutic for the treatment of infectious disease. In another embodiment, the peptides of the invention have been shown to reduce DPPIV activity, which has been shown to be related to a number of immune-related disorders, such as, AIDS and HIV disease progression (Blazquez et al. 1992; Vanham et al. 1993; Schols et al. 1998 Oravecz et al. 1995), Graves' disease (Eguchi et al. 1989; Nishikawa et al. 1995), and cancer (Stecca et al. 1997), such as lung and colon cancer, and diabetes (Hinke et al. 2000; Marguet et al. 2000). Further, DPPIV as an indicator of T-cell activation has been shown to fluctuate in parallel with several autoimmune diseases such as rheumatoid arthritis (Nakao et al., 1989) and autoimmune thyroiditis (Eguchi et al., 1989). DPPIV has been described as a marker that correlates well with the level of activity of these diseases. It has furthermore been studied as an indicator of disease progression in chronic progressive multiple sclerosis (Constantinescu et al., 1995). The peptides of the invention can be used in the treatment of such conditions.

Peptides of the Invention

Accordingly, the present invention provides isolated peptides having or comprising the amino acid sequence of TABLE 1 or an immunologically active analogue, derivative, or variant thereof. Also provided are pharmaceutically-acceptable salts, acid addition salts, and esters of the peptides, analogues, derivatives, and variants of the invention, including those described herein, such as conservative substitution, and, N and C terminus modifications and backbone modifications, as described herein. As used herein, an "isolated"

peptide of the invention is a peptide which either has no naturally-occurring counterpart or has been separated or purified from components which naturally accompany it. An isolated peptide of the invention can be obtained, for example, by expression of a recombinant nucleic acid encoding the peptide or by chemical synthesis. Because a peptide that is chemically synthesized is, by its nature, separated from the components that naturally accompany it, the synthetic peptide is "isolated".

In one aspect, the isolated peptide of the invention comprises the amino acid sequence having the formula: "$X_1X_2P$" (SEQ ID NO: 55), wherein: $X_1$ is selected from the group consisting of K, H, R, S, T, O, Cit, Hci, Dab, Dpr, or glycine based compounds with basic functional groups substituted on the N-terminal (e.g., NLys), hSer, Val(betaOH), or in another embodiment is selected from the group consisting of K, R, S, O, and Cit, or in another embodiment, selected from the group consisting of K, R, and S, or is R; and wherein $X_2$ is selected from the group consisting of V, I, K, P, and H. In one embodiment, the isolated peptide of the invention is SEQ. ID. NO. SEQ ID NO: 55. In another aspect, it is a peptide of up to 10 amino acids comprising an amino acid sequence of SEQ ID NO: 55. In one embodiment, the isolated peptide of SEQ ID NO: 55 is SEQ ID NOs: 8, 9, 26, 39, 40, 41, and 45-53, or an isolated peptide of up to 10 amino acids comprising said sequences. In another embodiment, the isolated peptide comprising SEQ ID NO: 55 is SEQ ID NO: 44, which is up to 13 amino acids.

In another embodiment, the invention provides an isolated peptide comprising the formula, "$X_1X_2X_3P$" (SEQ ID NO: 56) wherein $X_1$ is selected from the group consisting of K, H, R, S, T, O, Cit, Hci, Dab, Dpr, or glycine based compounds with basic functional groups substituted on the N-terminal (e.g., NLys), hSer, Val(betaOH), or in another embodiment selected from the group consisting of K, H, R, S, T, and O, or in another embodiment, K, H, R, S, and T, or in another embodiment, K, H, R, S and O, or in another embodiment, R, H, K and S; and wherein $X_2$ is selected from the group consisting of A, I, L, V, K, P, G, H, R, S, O, Dab, Dpr, Cit, Hci, Abu, Nva, Nle and where $X_2$ can be N-methylated, or in another embodiment, selected from the group consisting of A, I, L, V, K, P, G, H, and R, where it can be N-methylated; and wherein $X_3$ is selected from the group consisting of I, V, P, wherein in one embodiment, $X_3$ is not N-methylated. In one embodiment, the isolated peptide can be an amino acid sequence of up to 10 amino acids, comprising SEQ. ID. NO: 56, including SEQ ID NOs: 1, 3-7, 10-16, 18, 21-25, 27, 28, 31-39, 42, 43, or 47, or an isolated peptide of up to 11 amino acids comprising SEQ ID NO: 54. However, in one embodiment when SEQ ID NO: 56 is a hexamer, it is not SEQ ID NO: 2, or when in one embodiment, when it is a pentamer, it is not SEQ ID NO: 17. In one embodiment, the isolated peptide of the invention does not comprise a peptide comprising SEQ ID NOs: 2 or 17.

In another embodiment, the invention provides an isolated peptide comprising the peptide comprising the formula of SEQ ID NO:56 in a pentamer or hexamer. In one embodiment, said peptide is immunologically active.

In one embodiment, the isolated peptide of the invention comprises a peptide of formula, "$aX_1X_2X_3P$" (SEQ. ID. NO. 57) wherein $X_1$, $X_2$ and $X_3$ are defined as for SEQ ID NO: 56, and wherein "a" is selected from the group consisting of S, P, I, R, C, T, L, V, A, G, K, H, R, O, C, M, and F, or in another embodiment is selected from the group consisting of, S, P, I, R, C, T, L, V, A, G, K, H, R, O, C, and M, or in another embodiment is selected from the group consisting of, S, P, I, R, and C, or in another embodiment is S. In one embodiment, the isolated peptide comprises SEQ ID NO: 57, or is a peptide of up to 10 amino acids comprising said sequence. In another embodiment, the isolated peptide is SEQ ID NO: 4 or 47, or when it is a hexamer, SEQ ID NO: 39, or an isolated peptide up to 10 amino acids comprising said sequences.

In another embodiment, the isolated peptide of the invention comprises a peptide of formula, "$X_1X_2X_3Pb$" (SEQ ID NO: 58) wherein $X_1X_2X_3$ are as defined in SEQ ID NO: 56 and "b" is selected from the group consisting of A, A*, G, S, L, F, K, C, I, V, T, Y, R, H, O, and M, but in one embodiment not P, or in another embodiment selected from the group consisting of A, A*, G, S, L, F, and K, or in another embodiment selected from the group consisting of A, A*, G, S, L, K and C, or in one embodiment, selected from the group consisting of A, A*, G, S, L, and K. Wherein A* denotes a D amino acid of Alanine. In one embodiment, the isolated peptide is an amino acid of up to 10 amino acids comprising SEQ ID NO: 58. In one embodiment, the isolated peptide is or comprises SEQ ID NOs: 5-8, 10, 11, 13-16, 21-25, 27, 28, 31, 33-38 and 42-43. In another embodiment, the peptide is of SEQ ID NO: 58, wherein "b" is not P or Y, or not RIVPP (SEQ ID NO:17); or where $X_3$ is not G or not RIGPA, or $X_3$ is not Vx or not RIVxPA.

In one embodiment, the isolated peptide of the invention is or comprises a peptide similar to SEQ ID NO: 58, but wherein $X_1$ is instead selected from the group consisting of G, GG, or Cit, or wherein "b" is A, $X_2$ is I, $X_3$ is V, $X_1$ is G, GG, or Cit, or the peptide is SEQ ID NOs: 19, 20 or 36. In one embodiment, the isolated peptide comprises SEQ ID NO: 31. In another embodiment, the isolated peptide comprises a reverse sequence of SEQ ID NO:58, or comprises SEQ ID NO:30.

In one embodiment, the isolated peptide of the invention is or comprises a peptide having the amino acid sequence of SEQ ID NO: 29.

The peptide of the invention also provides an isolated peptide comprising the formula, "$a_1a_2 X_1X_2X_3P$" (SEQ ID NO:59), where $X_1$, $X_2$ and $X_3$ are as defined in SEQ ID NO: 56 and $a_1$ is selected from the group consisting of K, I R, H, O, L, V, A, and G, or in one embodiment, K and I, or in one embodiment K and $a_2$ is selected from the group consisting of S, P, R T, H, K, O, L, V, A, G, S, and I or in one embodiment, S, P, and R, or in another embodiment, S and P, or in another embodiment P. In one embodiment, $a_1$ is not acetylated, or where $a_1$ is K, K is not acetylated or not SEQ ID NO: 2. In one embodiment, the isolated peptide is or comprises SEQ ID NOs: 1 and 47 or a peptide of up to 10 amino acids comprising SEQ ID NO: 59.

In another embodiment, the isolated peptide of the invention is or comprises a peptide of the formula, "$a X_1X_2X_3Pb$" (SEQ ID NO: 60) where $X_1$, $X_2$ and $X_3$ are as defined in SEQ ID NO: 56 and where "a" is selected from the group consisting of S, R, K, H, O, T, I, L, V, A, G or in another embodiment, S, R and I, or in another embodiment S and R, and wherein "b" is selected from the group consisting of A, V, I, L, G, K, H, R, O, S, T, F or in another embodiment, A. In another embodiment, the peptide of SEQ ID NO: 60 is SEQ ID NO: 3, 12 or 39, or a peptide of up to 10 amino acids comprising SEQ ID NO: 60 or SEQ ID NO: 3, 12 or 39.

As used herein, a "peptide comprising an amino acid sequence of a sequence of TABLE 1" or a "peptide comprising an amino acid sequence of a sequence of TABLE 1" includes the peptide itself, obvious chemical equivalents thereto, isomers thereof (e.g., isomers, stereoisomers, retro isomers, retro-inverso isomers, all-[D] isomers, all-[L] isomers, or mixed [L] and [D] isomers thereof), conservative substitutions therein, precursor forms thereof, endoproteolytically-processed forms thereof, such as cleavage of single amino acids from N or C terminals or immunologically active metabolites of the peptides of the invention, pharmaceutically-acceptable salts and esters thereof, and other forms resulting from post-translational modification. Also included is any parent sequence, up to and including 10, 9, 8, 7, 6, 5 and 4 amino acids in length (cyclized, or linear, or branched from the core parent sequence), for which the specified sequence is a subsequence. A person skilled in the art would appreciate that where the peptide in the table is a trimer, it could be a subsequence of a 10, 9, 8, 7, 6, 5, and 4 mer, whereas if the peptide listed in TABLE 1 is a hexamer, it could be a subsequence of a 10, 9, 8, and 7 mer, but not a 5 or 4 mer. In addition, the invention comprises sequences that are greater than 10 mer, SEQ ID NOs: 44 and 54. Those modified peptides which retain the immunological activity of the peptides of the invention are encompassed within the scope of the present invention.

As further used herein, an "obvious chemical equivalent" of a peptide of the invention is a molecule which possesses the same desired activity, e.g immunological activity, as peptides described herein, and exhibits a trivial chemical different, or a molecule which is converted, under mild conditions, into a peptide of the invention (e.g., esters, ethers, reduction products, and complexes of the peptides of the invention).

Additionally, as used herein, "conservative substitutions" are those amino acid substitutions which are functionally equivalent to the substituted amino acid residue, either because they have similar polarity or steric arrangement, or because they belong to the same class as the substituted residue (e.g., hydrophobic, acidic, or basic). The term "conservative substitutions", as defined herein, includes substitutions having an inconsequential effect on the ability of the peptide of the invention to enhance innate immunity. Examples of conservative substitutions include the substitution of a polar (hydrophilic) residue for another (e.g., arginine/lysine, glutamine/asparagine, or threonine/serine); the substitution of a non-polar (hydrophobic) residue (e.g., isoleucine, leucine, methionine, phenylalanine, tyrosine, or valine) for another; the substitution of an acidic residue (e.g., aspartic acid or glutamic acid) for another; or the substitution of a basic residue (e.g., arginine, histidine, lysine or ornithine) for another.

The term "analogue", as used herein, includes any peptide having an amino acid sequence substantially identical to a sequence described herein, in which at least one residue has been conservatively substituted with a functionally-similar residue. An "analogue" has 60% or greater (preferably, 70% or greater, 80% or greater, 85% or greater, 90% or greater, 95% or greater, or 99%) amino-acid-sequence homology with an amino acid sequence of TABLE 1, and is a functional variant thereof. As further used herein, the term "functional variant" refers to the activity of a peptide that demonstrates an ability to enhance innate immunity or reduce DPPIV activity, as described herein. An "analogue" includes a variant of an amino acid of TABLE 1 that has an homologous three-dimensional conformation. An "analogue" further includes any pharmaceutically-acceptable salt of an analogue as described herein. A "variant" further includes any pharmaceutically-acceptable salt of a variant as described herein.

A "derivative", as used herein, refers to a peptide of the invention having one or more amino acids chemically derivatized by reaction of a functional side group. Exemplary derivatized molecules include, without limitation, peptide molecules in which free amino groups have been derivatized to form salts or amides, by adding acetyl groups, amine hydrochlorides, carbobenzoxy groups, chloroacetyl groups, formyl groups, p-toluene sulfonyl groups, or t-butyloxycarbonyl groups. Free hydroxyl groups may be derivatized to form O-acyl or O-alkyl derivatives. Furthermore, free carboxyl groups may be derivatized to form salts, esters (e.g., methyl and ethyl esters), or hydrazides. Thus, a "derivative" further includes any pharmaceutically-acceptable salt of a derivative as described herein.

In one embodiment of the present invention, the isolated peptide of the invention has a modified C-terminus and/or a modified N-terminus. For example, the isolated peptide may have an amidated C-terminus. For example, the amino terminus can be acetylated (Ac) or the carboxy terminus can be amidated ($NH_2$). However, in one embodiment of the invention, the peptides of the invention are not preferably acetylated if such a modification would result in loss of desired immunological activity. Amino terminus modifications include methylating (i.e., —$NHCH_3$ or —$NH(CH_3)_2$, acetylating, adding a carbobenzoyl group, or blocking the amino terminus with any blocking group containing, a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

In one embodiment backbone substitutions can be made, such as NH to $NCH_3$. The isolated peptide may also be a modification (e.g., a point mutation, such as an insertion or a deletion, or a truncation) of or comprising an amino acid sequence of TABLE 1. By way of example, the peptide may comprise an amino acid sequence of TABLE 1 as modified by at least one point insertion of a D amino acid as long as desired immunological activity is retained. In particular, proline analogs in which the ring size of the proline residue is changed from 5 members to 4, 6, or 7 members can be employed. Cyclic groups can be saturated or unsaturated, and if unsaturated, can be aromatic or non-aromatic.

One can replace the naturally occurring side chains of the 20 genetically encoded amino acids (or D amino acids) with other side chains with similar properties, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

Such substitutions can include but are not necessarily limited to: (1) non-standard positively charged amino acids, like: ornithine, Dab; 2,4-diaminobutyric acid, which is like ornithine minus one methylene group (or lysine minus two methylene groups), Dpr or Dapa; 2,3-diaminopropionic acid, which is like ornithine minus two methylene group (or lysine minus three methylene groups, or serine with an amino group instead of hydroxyl), Nlys; N-(4-aminobutyl)-glycine which has the lysine side chain attached to the "N-terminus", and compounds with aminopropyl or aminoethyl groups attached to the amino group of glycine. (2), Non-naturally occurring amino acids like arginine, no charge, such as, Cit; citrulline and Hci; citrulline with one more methylene group; (3) non-standard non-naturally occurring amino acids with OH (e.g., like serine), such as, hSer; homoserine (one more methylen group, Hyp; hydroxyproline, Val(betaOH); hydroxyvaline, Pen; penicillamin, (Val(betaSH); (4) proline derivatives, such as, D-Pro, such as, 3,4-dehydroproline, Pyr; pyroglutamine (proline with C=O in ring), Proline with fluorine substitutions on the ring, 1,3-thiazolidine-4-carboxylic acid (proline with S in ring); (5) Histidine derivative, such as, Thi; beta-(2-thienyl)-alanine; or (6) alkyl derivatives, such as, Abu; 2-aminobutyric acid (ethyl group on Calpha), Nva; norvaline (propyl group on Calpha), Nle; norleucine (butyl group on Calpha), Hol; homoleucine (propyl group on Calpha), Aib, alpha-aminoisobutyric acid (valine without methylene group). A person skilled in the art would appreciate that those substitutions that retain the immunological activity of the parent peptide/sequence.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can also cyclize the peptide by adding an N and/or C terminal cysteine and cyclizing the peptide through disulfide linkages or other side chain interactions.

One can also incorporate a desamino or descarboxy residue at the termini of the peptide, so that there is no terminal amino or carboxyl group, to decrease susceptibility to proteases or to restrict the conformation of the peptide.

Method of Making Peptides

The present invention contemplates peptides, including peptide analogues, derivatives, and variants, that are produced synthetically, generated recombinantly, or isolated from native cells. A peptide of the invention may be synthesized by methods commonly known to one skilled in the art (e.g., as described in *Modern Techniques of Peptide and Amino Acid Analysis* (New York: John Wiley & Sons, 1981; and Bodansky, M., *Principles of Peptide Synthesis* (New York: Springer-Verlag N.Y., Inc., 1984). Examples of methods that may be employed in the synthesis of the peptides of the invention include, but are not limited to, solid-phase peptide synthesis, solution or liquid-method peptide synthesis, and synthesis using any of the commercially-available peptide synthesizers. In one embodiment, a peptide of the invention is synthesized in vitro, e.g., by chemical means or in vitro translation of mRNA. In another embodiment, a peptide of the invention is produced recombinantly, using conventional techniques and cDNA encoding the peptide. The amino acid sequences of the present invention may further comprise coupling agents and protecting groups which are used in the synthesis of peptide sequences, and which are well known to one of skill in the art.

Peptide analogues, derivatives, and variants of the invention can be made by a wide variety of different mutagenesis techniques well known to those skilled in the art. These techniques can be found in any molecular biology laboratory manual, including, for example, Sambrook et al., *Molecular Cloning—A Laboratory Manual*, $2^{nd}$ ed. (Plainview, N.Y.: Cold Spring Harbor Press, 1989); or Ausubel et al., *Current Protocols in Molecular Biology* (John Wiley & Sons). Mutagenesis kits are also available from many commercial molecular biology suppliers. Methods are available to make site-directed, regio-specific, or random mutagenesis in the initial amino acid sequence. After the analogues, derivatives, and variants are produced, they can be screened for the desired ability to enhance innate immunity, as described herein.

Agents Reactive with Peptide

The present invention further provides an agent reactive with a peptide comprising an amino acid sequence of TABLE 1 or an analogue, derivative, or variant of thereof. As used herein, "reactive" means the agent has affinity for, binds to, or is directed against the peptide of the invention. As further used herein, an "agent" shall include a protein, polypeptide, peptide, nucleic acid (including DNA or RNA), a non-naturally occurring antibody, Fab fragment, $F(ab')_2$ fragment, molecule, compound, antibiotic, drug, and any combination(s) thereof. A Fab fragment is a univalent antigen-binding fragment of an antibody, which is produced by papain digestion. A $F(ab')_2$ fragment is a divalent antigen-binding fragment of an antibody, which is produced by pepsin digestion. Preferably, the agent of the present invention is labeled with a detectable marker or label. A non-naturally occurring antibody means, an antibody that is generated with the peptide associated with another compound, such as two C-terminal glycine residues and MAPS. MAPS Antigen is attached to the peptide of the present invention via 2 glycine residues inserted at the C-terminus of the peptide. The construct can then be administered to an animal, such as a rabbit and the antibody harvested using procedures well known in the art.

In one embodiment of the present invention, the agent reactive with the peptide of the invention is an antibody. As used herein, the antibody of the present invention may be polyclonal or monoclonal. In addition, the antibody of the present invention may be produced by techniques well known to those skilled in the art. Polyclonal antibody, for example, may be produced by immunizing a mouse, rabbit, or rat with a purified peptide of the invention. Monoclonal antibody then may be produced by removing the spleen from the immunized animal, and fusing the spleen cells with myeloma cells to form a hybridoma which, when grown in culture, will produce a monoclonal antibody. See, e.g., J. G. R. Hurrel, *Monoclonal Hybridoma Antibodies: Techniques and Applications* (Boca Raton, Fla.: CRC Press Inc., 1982).

The antibody of the invention may be labeled with a detectable marker or label. Labeling of an antibody may be accomplished using one of a variety of labeling techniques, including peroxidase, chemiluminescent labels known in the art, and radioactive labels known in the art. The detectable marker or label of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker or label may be a radioactive marker, including, for example, a radioisotope. The radioisotope may be any isotope that emits detectable radiation, such as $^{35}S$, $^{32}P$, $^{125}I$, $^{3}H$, or $^{14}C$. Radioactivity emitted by the radioisotope can be detected by techniques well known in the art. For example, gamma emission from the radioisotope may be detected using gamma imaging techniques, particularly scintigraphic imaging. Preferably, the agent of the present invention is a high-affinity antibody labeled with a detectable marker or label.

Isolated Nucleic Acid Molecules

In addition, the present invention provides an isolated nucleic acid molecule encoding a peptide comprising an amino acid sequence of TABLE 1 or an analogue, derivative, or variant thereof, including a conjugated peptide (e.g. a carrier-peptide construct) or other peptide, or a pro-peptide that metabolizes or cleaves to an immunologically active peptide of TABLE 1. Due to the degeneracy of the genetic code, the nucleic acid molecule of the invention includes a multitude of nucleic acid substitutions that will also encode a peptide of the invention. The present invention further provides a nucleic acid which hybridizes to the isolated nucleic acid molecule encoding an amino acid sequence of TABLE 1 or an analogue, derivative, or variant thereof.

The nucleic acid molecules of the present invention may be DNA or RNA. They may be prepared by a variety of techniques known to those skilled in the art, including, without limitation, automated synthesis of oligonucleotides using commercially-available oligonucleotide synthesizers, such as the Applied Biosystems Model 392 DNA/RNA synthesizer. In addition, the nucleic acid molecules of the present invention may be labeled with one or more detectable markers or labels. Labeling of the nucleic acid molecules may be accomplished using one of a number of methods known in the art—e.g., nick translation, end labeling, fill-in end labeling, polynucleotide kinase exchange reaction, random priming, or SP6 polymerase (for riboprobe preparation)—along with one of a variety of labels—e.g., radioactive labels, such as $^{35}$S, $^{32}$P, or $^{3}$H, or nonradioactive labels, such as biotin, fluorescein (FITC), acridine, cholesterol, or carboxy-X-rhodamine (ROX).

The present invention also provides a recombinant nucleic acid construct comprising a nucleic acid molecule of the invention operably linked to an expression vector. As used herein, an "expression vector" is a DNA construct containing a DNA sequence which is operably linked to a suitable control sequence capable of effecting the expression of the DNA in a suitable host. The vector may be, for example, a plasmid, a phage particle, or a potential genomic insert. As further used herein, the term "operably linked" describes a functional relationship between two DNA regions. Expression vectors suitable for use in the present invention comprise at least one expression control element (e.g., operator, promoter, lac system, leader sequence, termination codon, and/or polyadenylation signal) operably linked to the nucleic acid molecule encoding a peptide of the invention. In one embodiment, the expression vector is a eukaryotic expression vector that functions in eukaryotic cells (e.g., a retroviral vector, a vaccinia virus vector, an adenovirus vector, a herpes virus vector, or a fowl pox virus vector).

Once operably linked to a nucleic acid molecule of the invention, the expression vector may be introduced into a recipient cell by any in vivo or ex vivo means suitable for transfer of nucleic acid, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, viral vectors, naked DNA transfer, or any combination thereof. Recombinant viral vectors suitable for transfer of nucleic acid include, but are not limited to, vectors derived from the genomes of viruses such as retrovirus, HSV, adenovirus, adeno-associated virus, Semiliki Forest virus, cytomegalovirus, and vaccinia virus.

The present invention further provides at least one host cell comprising the recombinant nucleic acid construct of the invention. The host cell of the invention is transformed with the nucleic acid construct described herein. The host cell may be eukaryotic (e.g., an animal, plant, insect, or yeast cell) or prokaryotic (e.g., *E. coli*).

In addition, the present invention provides a method for producing a peptide comprising an amino acid sequence of TABLE 1 or an analogue, derivative, or variant thereof. The method comprises the steps of: (a) culturing at least one host cell comprising a recombinant nucleic acid construct, as described herein, under conditions allowing expression of the peptide; and (b) recovering the peptide from the at least one host cell or from the culture medium thereof. The recombinant peptide can be recovered as a crude lysate; it can also be purified by standard protein purification procedures known in the art, including, without limitation, affinity and immunoaffinity chromatography, differential precipitation, gel electrophoresis, ion-exchange chromatography, isoelectric focusing, size-exclusion chromatography, and the like.

Pharmaceutical Composition

The present invention further provides a pharmaceutical composition comprising a peptide comprising an amino acid sequence of TABLE 1 or SEQ ID NOs: 1, 3-16, or 18-60, or an analogue, derivative, or variant thereof (which includes a pharmaceutically-acceptable salt, acid addition salt or ester of any of the foregoing), in combination with at least one pharmaceutically-acceptable carrier, diluent, or excipient. The pharmaceutically-acceptable carrier, diluent, or excipient must be "acceptable" in the sense of being compatible with the other ingredients of the composition, and not deleterious to the recipient thereof. Examples of acceptable pharmaceutical carriers, diluents, and excipients include, without limitation, carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition of the invention, as described herein, may be conveniently presented in unit dosage.

Uses

The peptides of the invention have been shown to have therapeutic utility in enhancing innate immunity. The enhancement of innate immunity is demonstrated by the lack of antimicrobial activity (Example 2) and the protection against infection in in vivo models (Examples 3 and 4) and also by the DPPIV assays of Example 5. Accordingly, the present invention also provides a method for treating and/or preventing infection in a subject. As used herein, the "subject" is a bird (e.g., a chicken, turkey, etc.) or a mammal (e.g., a cow, dog, human, monkey, mouse, pig, rat, etc.). In one embodiment, the subject is a human. The subject may have, or be at risk of having, an infection. By way of example, the infection may be a microbial infection. Microbial infections which may be treated by the method of the present invention include, without limitation, infection by a bacterium, infection by a fungus, infection by a parasite, and infection by a virus.

Most bacterial pathogens are present in the general environment, or in the host's normal bacterial flora. Bacteria have evolved the ability to cause severe disease by acquiring different mechanisms (called virulence factors) which enable them to colonize, disseminate within, and invade host tissues. When these pathogenicity factors are suppressed, bacteria are no longer able to maintain themselves in host tissues, and, therefore, cannot cause disease. Exemplary bacteria which may be treated by the method of the present invention include, without limitation, *E. coli, Klebsiella pneumoniae, Pseudomonas aeruginosa, Salmonella* spp. (e.g., *Salmonella typhimurium*), *Staphylococcus aureus, Streptococcus* spp., and vancomycin-resistant *enterococcus*.

*Pseudomonas aeruginosa* is a ubiquitous Gram-negative bacterium that is noted for its environmental versatility, its ability to cause disease in susceptible individuals, and its resistance to antibiotics. It is a versatile organism that grows in soil, marshes, and coastal marine habitats, and on plant and animal tissues. The most serious complication of cystic fibrosis is respiratory tract infection by *P. aeruginosa*. Cancer and burn patients also commonly suffer serious infections by this organism, as do certain other individuals with immune system deficiencies. Unlike many environmental bacteria, *P. aeruginosa* has a remarkable capacity to cause disease in susceptible hosts.

*Staphylococcus aureus* is a Gram-positive spherical bacterium, about 1 micrometer in diameter, that thrives in microscopic clusters. It is one of the most important human pathogens, causing both community-acquired and nosocomial infections that range from endocarditis to pneumonia. Although *S. aureus* is generally classified as an extracellular pathogen, recent data have revealed its ability to infect various types of host cells, e.g., both professional phagocytes and non-phagocytes, including endothelial cells, fibroblasts, and others. This invasion is initiated by the adherence of *S. aureus* to the cell surface, a process in which staphylococcal fibronectin-binding proteins play a prominent role. Phagocytosed *S. aureus* can either induce apoptosis of the host cell or survive for several days in the cytoplasm—which is thought to be devoid of anti-staphylococcal effector mechanisms.

*S. aureus* colonizes nasal passages, skin surfaces, mucous membranes, and areas around the mouth, genitals, and rectum. *S. aureus* may cause superficial skin lesions, such as boils, sties, and furuncles. More serious infections include pneumonia, mastitis, phlebitis, meningitis, and urinary tract infections; deep-seated infections include osteomyelitis and endocarditis.

Exemplary fungi which may be treated by the method of the present invention include, without limitation, moulds, yeasts, and higher fungi. All fungi are eukaryotic, and have sterols, but not peptidoglycan, in their cell membranes. Fungal infections, or mycoses, are classified according to the degree of tissue involvement and the mode of entry into the host. In the immunocompromised host, a variety of non-pathogenic fungi, or fungi that are normally mild, can cause potentially fatal infections.

Parasites are organisms that derive nourishment and protection from other living organisms (known as hosts). They may be transmitted from animals to humans, from humans to humans, or from humans to animals. Several parasites have emerged as significant causes of food-borne and water-borne disease. They may be transmitted from host to host through consumption of contaminated food and water, or through ingestion of a substance that has come into contact with the stool (feces) of an infected person or animal. Parasites live and reproduce within the tissues and organs of infected human and animal hosts, and are often excreted in feces. There are different types of parasites, ranging in size from tiny, single-celled, microscopic organisms (protozoa), to larger, multi-cellular worms (helminths) that may be seen without a microscope. Examples of common parasites which may be treated by the method of the present invention include, without limitation, *Giardia duodenalis, Cryptosporidium parvum, Cyclospora cayetanensis,* and *Toxoplasma gondii.*

Viruses are unlike fungi and bacteria, lacking many of the attributes of free-living cells. A single virus particle is a static structure, quite stable and unable to change or replace its parts. Only when associated with a cell does a virus become capable of replicating and acquiring some of the attributes of a living system. Viruses cause numerous diseases, including such upper respiratory tract infections (URTIs) as the common cold and pharyngitis (sore throat). Other examples of viruses which may be treated by the method of the present invention include, without limitation, viruses associated with AIDS, avian flu, chickenpox, cold sores, common cold, gastroenteritis (especially in children), glandular fever, influenza, measles, mumps, pharyngitis, pneumonia, rubella, SARS, and lower respiratory tract infection (e.g., respiratory syncytial virus, or RSV)).

The inventors have demonstrated herein that peptides comprising the amino acid sequence of TABLE 1 or SEQ ID NO: 1, 3-16, 18-60, or analogue, derivative, or variant thereof or obvious chemical equivalent thereof have efficacy in the prevention and/or treatment of infection. Accordingly, the present method of treating and/or preventing infection in a subject comprises administering to the subject a peptide comprising the amino acid sequence of TABLE 1 or SEQ ID NO: 1, 3-16, 18-60, or analogue, derivative, or variant thereof or obvious chemical equivalent thereof. It is within the confines of the present invention that the peptide of the invention may be linked to another agent or administered in combination with another agent, such as an antibiotic (e.g., penicillin, methicillin, or vancomycin), in order to increase the effectiveness of the treatment and/or prevention of infection, and/or increase the efficacy of targeting.

In one embodiment of the present invention, the peptide of the invention comprises the amino acid sequence of TABLE 1 or SEQ ID NO: 1, 3-16, 18-60, or analogue, derivative, or variant thereof or obvious chemical equivalent thereof. In another embodiment, the peptide of the invention modulates innate immunity in the subject, thereby treating and/or preventing the infection in the subject. The innate immune response is the front line response to a pathogen encounter. It comprises a multiplicity of mechanisms to prevent development of infectious disease. One such mechanism involves the priming and recruitment of immune effector cells.

In one embodiment, the peptides of the invention can enhance innate immunity or the innate immune response, while limiting inflammation.

In another embodiment, the peptides of the invention have been shown to be modulators of DPPIV activity. They have been shown to reduce DPPIV activity. As such, they would be useful in the screening of subjects who may benefit from administration of the peptides to treat a particular immunological condition, comprising taking a sample from a subject suspected or known to have a DPPIV-related condition, incubating it together with a peptide of the invention and a DPPIV substrate and then monitoring the effect of the peptide on DPPIV activity in comparison to a control wherein a reduction in activity would indicate the potential benefit of administration of the peptide to the subject to treat a DPPIV-related condition. In another embodiment modulation of DPPIV activity in the presence of the peptide as compared to the control can be indicative of a DPPIV-related condition. As such, the peptides of the invention can be used in the diagnosis of DPPIV-related conditions. In another aspect the peptides of the invention would be useful in the treatment of a number of immunological disorders, such as DPPIV-related disorder, such as: HIV/AIDS, Grave's disease, cancer (such as lung and colon cancer), diabetes, and autoimmune disorders such as rheumatoid arthritis and multiple sclerosis.

Administration

In accordance with the method of the present invention, a peptide of the present invention as described herein may be administered to the subject directly, in an amount effective to treat and/or prevent infection in the subject and or to treat or prevent a DPPIV-related condition, e.g. a therapeutic effective amount. Similarly, a peptide as described herein may be administered to the subject indirectly, by administering to the subject a nucleic acid sequence encoding the peptide, in a manner permitting expression of the peptide in the subject, and in an amount effective to treat and/or prevent infection.

Furthermore, a peptide of the invention, or a nucleic acid molecule encoding same, may be administered to a subject in an amount effective to treat the infection in the subject. As used herein, the phrase "effective to treat the infection" means effective to ameliorate or minimize the clinical impairment or symptoms resulting from infection (by a bacterium, fungus, parasite, virus, etc.). For example, where the subject is infected with a microbe, the amount of peptide (or nucleic acid encoding same) which is effective to treat the microbial infection is that which can ameliorate or minimize the symptoms of the microbial infection, including, without limitation, headache, stiff neck, anorexia, nausea, vomiting, diarrhea, abdominal discomfort, acute renal failure, changing manifestations of ischemic damage to multiple organs, fever, and thrombocytopenia. The amount of peptide (or nucleic acid encoding same) effective to treat an infection in a subject will vary depending on the particular factors of each case, including the subject's weight and the severity of the subject's condition. The appropriate amount of peptide (or nucleic acid encoding same) can be readily determined by the skilled artisan. Similarly the amount effective to treat a DPPIV-related condition can vary depending on a number of similar factors known to a person skilled in the art.

Similarly, in the method of the present invention, a peptide of the invention, or a nucleic acid molecule encoding same, may also be administered to a subject at risk of developing an infection, in an amount effective to prevent the infection in the subject. As used herein, the phrase "effective to prevent the infection" includes effective to hinder or prevent the development or manifestation of clinical impairment or symptoms resulting from infection (by a bacterium, fungus, parasite, virus, etc.). The amount of peptide (or nucleic acid encoding same) effective to prevent an infection in a subject will vary depending on the particular factors of each case, including the subject's sex, weight and the severity of the subject's condition, nature of condition, site of infection, and mode of administration. The appropriate amount of peptide (or nucleic acid encoding same) can be readily determined by the skilled artisan.

The peptide of the invention, or the nucleic acid sequence encoding same, as disclosed herein, may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, intranasal administration, pulmonary administration (e.g., intratracheal administration), and administration by osmotic pump. In one embodiment, the method of administration is parenteral administration, by intravenous or subcutaneous injection.

For oral administration, the formulation of the peptide (or nucleic acid encoding same) may be presented as capsules, tablets, powders, granules, or as a suspension or liquid. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation may be further presented with dibasic calcium phosphate anhydrous or sodium starch glycolate. Finally, the formulation may be presented with lubricants, such as talc or magnesium stearate.

For parenteral administration, the peptide (or nucleic acid encoding same) may be combined with a sterile aqueous solution, which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation also may be delivered by any mode of injection, including any of those described herein.

For transdermal administration, the peptide (or nucleic acid encoding same) may be combined with skin penetration enhancers, such as propylene glycol, polyethylene glycol, isopropanol, ethanol, oleic acid, N-methylpyrrolidone, and the like, which increase the permeability of the skin to the peptide or nucleic acid, and permit the peptide or nucleic acid to penetrate through the skin and into the bloodstream. The composition of enhancer and peptide or nucleic acid also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The peptide or nucleic acid may be administered transdermally, at or near the site on the subject where the infection may be localized. Alternatively, the peptide or nucleic acid may be administered transdermally at a site other than the affected area, in order to achieve systemic administration.

For intranasal administration (e.g., nasal sprays) and/or pulmonary administration (administration by inhalation), formulations of the peptide or nucleic acid, including aerosol formulations, may be prepared in accordance with procedures well known to persons of skill in the art. Aerosol formulations may comprise either solid particles or solutions (aqueous or non-aqueous). Nebulizers (e.g., jet nebulizers, ultrasonic nebulizers, etc.) and atomizers may be used to produce aerosols from solutions (e.g., using a solvent such as ethanol); metered-dose inhalers and dry-powder inhalers may be used to generate small-particle aerosols. The desired aerosol particle size can be obtained by employing any one of a number of methods known in the art, including, without limitation, jet-milling, spray drying, and critical-point condensation.

Pharmaceutical compositions for intranasal administration may be solid formulations (e.g., a coarse powder), and may contain excipients (e.g., lactose). Solid formulations may be administered from a container of powder held up to the nose, using rapid inhalation through the nasal passages. Compositions for intranasal administration may also comprise aqueous or oily solutions of nasal spray or nasal drops. For use with a sprayer, the formulation of peptide or nucleic acid may comprise an aqueous solution and additional agents, including, for example, an excipient, a buffer, an isotonicity agent, a preservative, or a surfactant. A nasal spray may be produced, for example, by forcing a suspension or solution of the peptide or nucleic acid through a nozzle under pressure.

Formulations of the peptide or nucleic acid for pulmonary administration may be presented in a form suitable for delivery by an inhalation device, and may have a particle size effective for reaching the lower airways of the lungs or sinuses. For absorption through mucosal surfaces, including the pulmonary mucosa, the formulation of the present invention may comprise an emulsion that includes, for example, a bioactive peptide, a plurality of submicron particles, a mucoadhesive macromolecule, and/or an aqueous continuous phase. Absorption through mucosal surfaces may be achieved through mucoadhesion of the emulsion particles.

Pharmaceutical compositions for use with a metered-dose inhaler device may include a finely-divided powder containing the peptide or nucleic acid as a suspension in a non-aqueous medium. For example, the peptide or nucleic acid may be suspended in a propellant with the aid of a surfactant (e.g., sorbitan trioleate, soya lecithin, or oleic acid). Metered-dose inhalers typically use a propellant gas (e.g., a chlorofluorocarbon, a hydrochlorofluorocarbon, a hydrofluorocarbon, or a hydrocarbon) stored in a container (e.g., a canister) as a mixture (e.g., as a liquefied, compressed gas). Inhalers require actuation during inspiration. For example, actuation of a metering valve may release the mixture as an aerosol. Dry-powder inhalers use breath-actuation of a mixed powder.

The peptide or nucleic acid of the present invention also may be released or delivered from an osmotic mini-pump or other timed-release device. The release rate from an elementary osmotic mini-pump may be modulated with a microporous, fast-response gel disposed in the release orifice. An osmotic mini-pump would be useful for controlling release, or targeting delivery, of the peptide or nucleic acid.

In accordance with methods described herein, the peptide of the invention may be administered to a subject by introducing to the subject the peptide itself, or by introducing to the subject a nucleic acid encoding the peptide in a manner permitting expression of the peptide. Accordingly, in one embodiment of the present invention, infection in a subject may be treated or prevented by administering to the subject an amount of a peptide of the invention. In a further embodiment of the present invention, infection in the subject may be treated or prevented by administering to the subject a nucleic acid sequence encoding a peptide of the invention, in a manner permitting expression of the peptide in the subject.

The peptides of the present invention may be administered or introduced to a subject by known techniques used for the introduction of proteins and other drugs, including, for example, injection and transfusion. Where an infection is localized to a particular portion of the body of the subject, it may be desirable to introduce the therapeutic peptide directly to that area by injection or by some other means (e.g., by introducing the peptide into the blood or another body fluid). The amount of peptide to be used is an amount effective to treat and/or prevent the infection in the subject, as defined above, and may be readily determined by the skilled artisan.

In the method of the present invention, the peptide also may be administered or introduced to the subject by introducing into a sufficient number of cells of the subject a nucleic acid encoding the peptide, in a manner permitting expression of the peptide. The amount of nucleic acid encoding the therapeutic peptide is an amount that will produce the peptide in an amount effective to treat and/or prevent infection, as defined above, in the subject. This amount may be readily determined by the skilled artisan.

Nucleic acid encoding the peptide of the present invention may be introduced to the subject using conventional procedures known in the art, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, naked DNA transfer, or any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus.

It is also within the confines of the present invention that a nucleic acid encoding a peptide of the invention may be introduced into suitable cells in vitro, using conventional procedures, to achieve expression of the therapeutic peptide in the cells. Cells expressing the peptide then may be introduced into a subject to treat and/or prevent infection in vivo. In such an ex vivo gene therapy approach, the cells are preferably removed from the subject, subjected to DNA techniques to incorporate nucleic acid encoding the therapeutic peptide, and then reintroduced into the subject.

It is also within the confines of the present invention that a formulation containing a peptide of the invention, or a nucleic acid encoding same, may be further associated with a pharmaceutically-acceptable carrier, diluent, or excipient, thereby comprising a pharmaceutical composition. Pharmaceutical compositions of the invention, and exemplary carriers, diluents, and excipients, are described above.

The formulations of the present invention may be prepared by methods well-known in the pharmaceutical arts. For example, the peptide of the invention, or a nucleic acid encoding same, may be brought into association with a carrier, diluent, or excipient, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the peptide of the present invention, or a nucleic acid molecule encoding same, to a subject, in order to treat and/or prevent infection. The peptide or nucleic acid is provided in an amount that is effective to treat and/or prevent infection in a subject to whom the pharmaceutical composition is administered. This amount may be readily determined by the skilled artisan, as described above.

Diagnostics and Screening Assays

The present invention provides a method for diagnosing a subject who is suspected of having an innate immune condition, or DPPIV-related condition, for predicting whether a subject would be responsive to treatment with a peptide of the invention, such as those listed in TABLE 1, or an analogue, derivative or variant thereof, and to screening for agents that would modulate (e.g., enhance, inhibit or mimic) the immunological effect of the peptides of the invention. In another embodiment, the invention provides methods for screening for immunologically active analogues, derivatives, and variants of the peptides of the invention or those listed in TABLE 1 or to immunologically active modifications thereof.

In one embodiment, a method for predicting whether a patient with a immunological disorder, such as an innate immune-related condition would be responsive to treatment with a peptide of the invention comprises obtaining a biological sample from the subject, administering a peptide of the invention to said sample, and monitoring levels of a predetermined marker that is indicative of the condition, such as DPPIV for a DPPIV-related condition, an inflammatory biomarker for an infection, cell viability or bacterial load, in comparison to a positive and/or negative control. The positive control can be a sample from a subject with a known immunological condition. A negative control can be a sample from the same subject that is not administered the peptide. If the peptide modulates the activity, level of marker, or cell viability in relation to the control, the subject may have such immunological disorder and may benefit from treatment with the peptide.

More particularly, in one aspect of the invention, if the subject has or is suspected of having a DPPIV-related condition, then monitoring DPPIV activity as the marker for the condition would be appropriate. In one aspect, reduction of DPPIV activity in comparison to the control would be indicative that the subject would be responsive to treatment with the peptide. Alternatively, if the subject has or was suspected of having an infection, then obtaining a sample from the patient, monitoring it for pathogen load or cell viability in comparison to a sample from the patient after administration of the peptide, wherein pathogen load is less or cell viability is higher in the patient after administration of the peptide, is indicative that the subject would benefit from peptide treatment or has an immunological disorder.

In another embodiment, if one wishes to see whether a peptide or modification of a peptide of TABLE 1 or other agent would have the same immunological activity as the peptide of the invention, one can monitor the effect of the peptide on DPPIV activity in comparison to the reference peptide with known modulatory affects, on a sample (either from a mouse infected with an agent or a known DPPIV-related condition), or to monitor prevention, administration of the peptide or agent to a sample, inducing said infection or DPPIV-related condition in said sample and then monitoring whether the peptide modulated or inhibited development of said infection or DPPIV-related condition, or immune response. Said sample can be an animal model, wherein induction of the condition or infection is done in an accepted animal model in accordance with ethical guidelines and then the animal or appropriate biological sample of the animal is screened for effect of the peptide.

The present invention further provides a method for predicting whether a subject would be responsive to treatment for a microbial infection wherein the treatment comprises administering to the subject a peptide comprising an amino acid sequence of TABLE 1 or an analogue, derivative, or variant thereof. The method includes assaying a diagnostic sample of the subject for one or more biomarkers (such as an inflammatory biomarker), wherein the presence of at least one biomarker (such as an inflammatory biomarker) is indicative that the subject would be responsive to the treatment.

As used herein a "biomarker" or "marker is any suitable biomarker known to be, or recognized as being, related to the condition (e.g. immune condition, infection, inflammatory condition, DPPIV-related condition, innate immune condition), and includes any molecule derived from a gene (e.g., a transcript of the gene), a sense (coding) or antisense (non-coding) probe sequence derived from a gene, or a partial-length or full-length translation product of a gene, or an antibody thereto, which can be used to monitor a condition, disorder, or disease associated with the immune response, innate immune response, inflammation, and/or a DPPIV-related condition.

According to the method of the present invention, the diagnostic sample of a subject may be assayed in vitro or in vivo. Where the assay is performed in vitro, a diagnostic sample from the subject may be removed using standard procedures. The diagnostic sample may be tissue, including any muscle tissue, skin tissue, or soft tissue, which may be removed by standard biopsy. In addition, the diagnostic sample may be a bodily fluid, including blood, saliva, serum, or urine. The subject or patient may be known to have a microbial infection or other immunological disorder such as a DPPIV-related condition, suspected of having a microbial infection or other immunological condition, such as an innate immune condition or DPPIV-related condition, or believed not to have a microbial infection or other immunological condition, such as an innate-immune condition, or DPPIV-related condition.

In accordance with the method of the present invention, a diagnostic sample of the subject may be assayed for expression of one or more desired markers. As used herein, "expression" means the transcription of an inflammatory-marker gene into at least one mRNA transcript, or the translation of at least one mRNA into a marker protein. Accordingly, a diagnostic sample may be assayed for marker expression by assaying for a marker protein, marker cDNA, or marker mRNA. The appropriate form of the marker will be apparent based on the particular techniques discussed herein.

Protein to be assayed may be isolated and purified from the diagnostic sample of the subject or patient using standard methods known in the art, including, without limitation, extraction from a tissue (e.g., with a detergent that solubilizes the protein) where necessary, followed by affinity purification on a column, chromatography (e.g., FPLC and HPLC), immunoprecipitation (with an antibody to an inflammatory marker of interest), and precipitation (e.g., with isopropanol and a reagent such as Trizol). Isolation and purification of the protein may be followed by electrophoresis (e.g., on an SDS-polyacrylamide gel). It is contemplated that the diagnostic sample may be assayed for expression of any or all forms of marker protein (including precursor, endoproteolytically-processed forms, and other forms resulting from post-translational modification). Nucleic acid may be isolated from a diagnostic sample using standard techniques known to one of skill in the art.

In accordance with the method of the present invention, a diagnostic sample of a subject may be assayed for marker expression, and marker expression may be detected in a diagnostic sample, using assays and detection methods readily determined from the known art (e.g., immunological techniques, hybridization analysis, fluorescence imaging techniques, and/or radiation detection), as well as any assays and detection methods disclosed herein (e.g., immunoprecipitation, Western blot analysis, etc.). For example, a diagnostic sample of a subject may be assayed for marker expression using an agent reactive with an inflammatory marker. As used herein, "reactive" means the agent has affinity for, binds to, or is directed against the marker. As further used herein, an "agent" shall include a protein, polypeptide, peptide, nucleic acid (including DNA or RNA), antibody, Fab fragment, F(ab')$_2$ fragment, molecule, compound, antibiotic, drug, and any combination(s) thereof. Preferably, the agent of the present invention is labeled with a detectable marker or label, in accordance with techniques described herein. In one embodiment of the present invention, the agent reactive with a marker is an antibody.

Where the agent of the present invention is an antibody reactive with the desired marker, a diagnostic sample taken from the subject may be purified by passage through an affinity column which contains antibody to the marker, attached as a ligand to a solid support (e.g., an insoluble organic polymer in the form of a bead, gel, or plate). The antibody attached to the solid support may be used in the form of a column. Examples of suitable solid supports include, without limitation, agarose, cellulose, dextran, polyacrylamide, polystyrene, sepharose, and other insoluble organic polymers. The antibody to the marker may be further attached to the solid support through a spacer molecule, if desired. Appropriate binding conditions (e.g., temperature, pH, and salt concentration) for ensuring binding of the agent and the antibody may be readily determined by the skilled artisan. In a preferred embodiment, the antibody to the marker is attached to a sepharose column, such as Sepharose 4B.

Additionally, where the agent is an antibody, a diagnostic sample of the subject may be assayed for expression of the immunological marker using binding studies that utilize one or more antibodies immunoreactive with the marker, along with standard immunological detection techniques. For example, the marker protein eluted from the affinity column may be subjected to an ELISA assay, Western blot analysis, flow cytometry, or any other immunostaining method employing an antigen-antibody interaction. Preferably, the diagnostic sample is assayed for marker expression using Western blotting.

Alternatively, a diagnostic sample of a subject may be assayed for marker expression using hybridization analysis of nucleic acid extracted from the diagnostic sample taken from the subject. According to this method of the present invention, the hybridization analysis may be conducted using Northern blot analysis of mRNA. This method also may be conducted by performing a Southern blot analysis of DNA using one or more nucleic acid probes which hybridize to nucleic acid encoding the marker. The nucleic acid probes may be prepared by a variety of techniques known to those skilled in the art, including, without limitation, the following: restriction enzyme digestion of marker nucleic acid; and automated synthesis of oligonucleotides having sequences which correspond to selected portions of the nucleotide sequence of the marker nucleic acid, using commercially-available oligonucleotide synthesizers, such as the Applied Biosystems Model 392 DNA/RNA synthesizer.

Nucleic acid probes used in the present invention may be DNA or RNA, and may vary in length from about 8 nucleotides to the entire length of the inflammatory-marker nucleic acid. In addition, the nucleic acid probes of the present invention may be labeled with one or more detectable markers or labels. Labeling of the nucleic acid probes may be accomplished using one of a number of methods known in the art, including any of those described herein. Combinations of two or more nucleic acid probes (or primers), corresponding to different or overlapping regions of the marker nucleic acid, also may be used to assay a diagnostic sample for marker expression, using, for example, PCR or RT-PCR.

The detection of marker expression in the method of the present invention may be followed by an assay to measure or quantify the extent of marker expression in a diagnostic sample of a subject. Such assays are well known to one of skill in the art, and may include immunohistochemistry/immunocytochemistry, flow cytometry, mass spectroscopy, Western blot analysis, or an ELISA for measuring amounts of marker protein. For example, to use an immunohistochemistry assay, histological (paraffin-embedded) sections of tissue may be placed on slides, and then incubated with an antibody against a marker. The slides then may be incubated with a second antibody (against the primary antibody), which is tagged to a dye or other calorimetric system (e.g., a fluorochrome, a radioactive agent, or an agent having high electron-scanning capacity), to permit visualization of the marker present in the sections.

The present invention is described in the following Examples, which are set forth to aid in the understanding of the invention, and should not be construed to limit in any way the scope of the invention as defined in the claims which follow thereafter.

EXAMPLES

Example 1

Peptide Synthesis

The peptides in TABLE 1 were synthesized using a solid phase peptide synthesis technique.

All the required Fmoc-protected amino acids were weighed in three-fold molar excess relative to the 1 mmole of peptide desired. The amino acids were then dissolved in Dimethylformaide (DMF) (7.5 ml) to make a 3 mMol solution. The appropriate amount of Rink amide MBHA resin was weighed taking in to account the resin's substitution. The resin was then transferred into the automated synthesizer reaction vessel and was pre-soaked with Dichloromethane (DCM) for 15 minutes.

The resin was de-protected by adding 25% piperidine in DMF (30 ml) to the resin and mixing for 20 minutes. After de-protection of the resin the first coupling was made by mixing the 3 mMol amino acid solution with 4 mMol 2-(1H-benzotriazole-1-yl)-1,1,3,3-tetramethyluronium hexafluorophosphate (HBTU) and 8 mMol N,N-diisopropylethylamine (DIEPA). The solution was allowed to pre-activate for 5 minutes before being added to the resin. The amino acid was allowed to couple for 45 minutes.

After coupling the resin was thoroughly rinsed with DMF and Dimethylacetamide (DMA). The attached Fmoc protected amino acid was deprotected in the same manner described above and the next amino acid was attached using the same coupling scheme AA:HBTU:DIEPA.

After the completion of the synthesis the peptide was cleaved from the resin with the use of a cleavage cocktail containing 97.5% Trifluoroacetic acid (TFA) and 2.5% water. The resin was allowed to swim in the cleavage cocktail for 1½ hours. The solution was then filtered by gravity using a Buchner funnel and the filtrate was collected in a 50 ml centrifugation tube. The peptide was isolated by precipitating with chilled diethyl ether. After centrifuging and decanting diethyl ether the crude peptide was washed with diethyl ether once more before being dried in a vacuum desiccator for 2 hours. The peptide was then dissolved in de-ionized water (10 ml), frozen at $-80°$ C. and lyophilized. The dry peptide was then ready for HPLC purification.

Due to the hydrophilic nature of these peptides the diethyl ether peptide isolation did not work. Therefore a chloroform extraction was required. The TFA was evaporated and the resulting peptide residue was dissolved in 10% acetic acid (15 ml). The impurities and scavengers were removed from the acetic acid peptide solution by washing the solution twice with chloroform (30 ml). The aqueous peptide solution was then frozen at $-80°$ C. and lyophilized resulting in a powdered peptide ready for HPLC purification.

Peptides SEQ ID NOs: 33 and 34 each contained one N-methyl amino acid. This coupling was carried out by combining the N-methyl amino acid, PyBroP and N-hydroxybenzotriazole*$H_2O$ (HOBt) and DIEPA solutions together in the RV containing the resin. After allowing to couple for 45 minutes the N-methyl amino acid was then doubled coupled to ensure complete coupling. It was observed that the coupling following the N-methyl amino acid was not fully complete. Therefore this coupling was performed using N,N,N',N'-Tetramethyl-O-(7-azabenzotriazol-1-yl)uronium hexafluorophosphate (HATU) instead of HBTU. This still resulted in a crude peptide that typically contained two impurities totaling 30-40% of the total purity. The peptide was purified under modified HPLC conditions to isolate the pure peptide peak away from the closely eluting impurities.

Example 2

Non-Antimicrobial Activity

Bacteria (*S. aureus* 25923) were seeded into wells containing peptide (200 μM), vehicle (Tris), or antibiotic (erythromycin; 120 µg/ml). The bacteria were allowed to grow for 2 hours. Thereafter, bacterial viability was determined utilizing a WST-1 colorimetric viability assay (catalogue number 1 644 807; Roche Diagnostics). DMEM and DMEM+WST-1 were included as background controls. As shown in FIGS. 1A and B, the peptide of SEQ ID NOs: 5 and 47 clearly show a lack of activity, as compared with an antibiotic control.

Example 3

In Vivo Protection

Figure 2A:
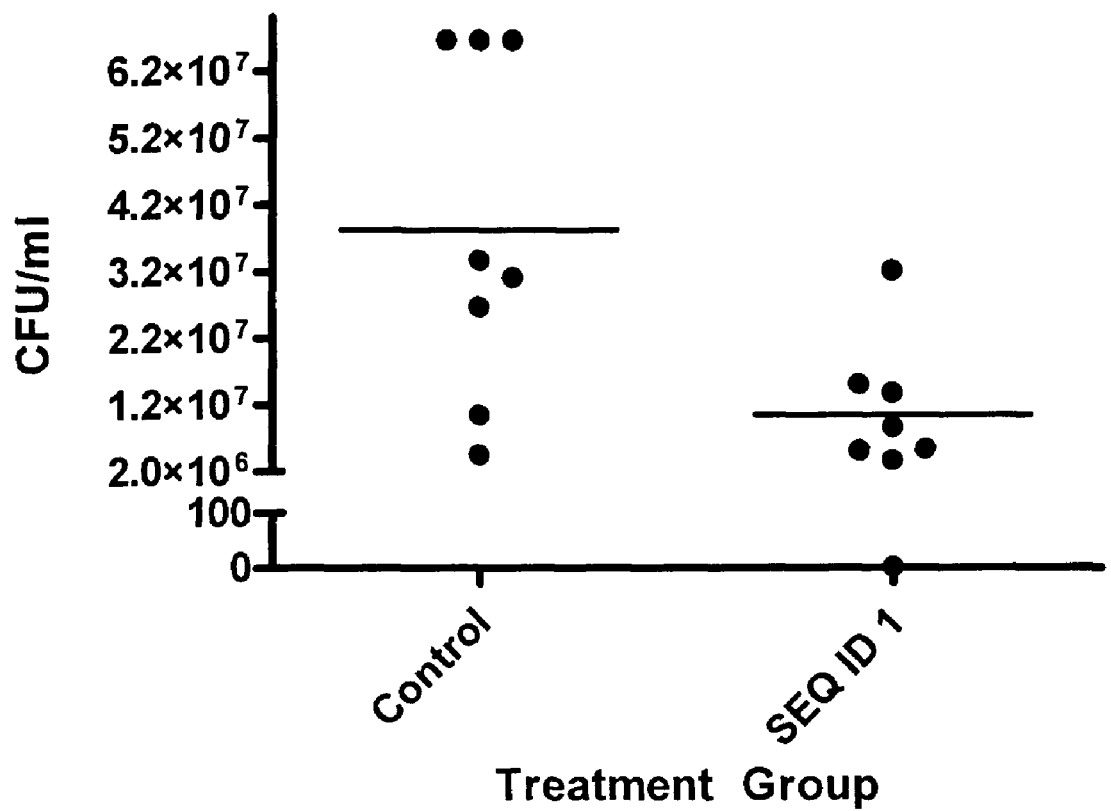
FIGS. 2 A-G depicts the results of the experiment described in Example 3. The graph shows colony-forming units per ml (CFU/ml) on the Y-axis, and treatment group (control=no peptide; SEQ ID NOs: 1, 4, 5, 6, 45 and 47=treatment with a peptide having the respective amino acid sequence) on the X-axis. The bacterial count of individual mice is shown.
Figure 2B:
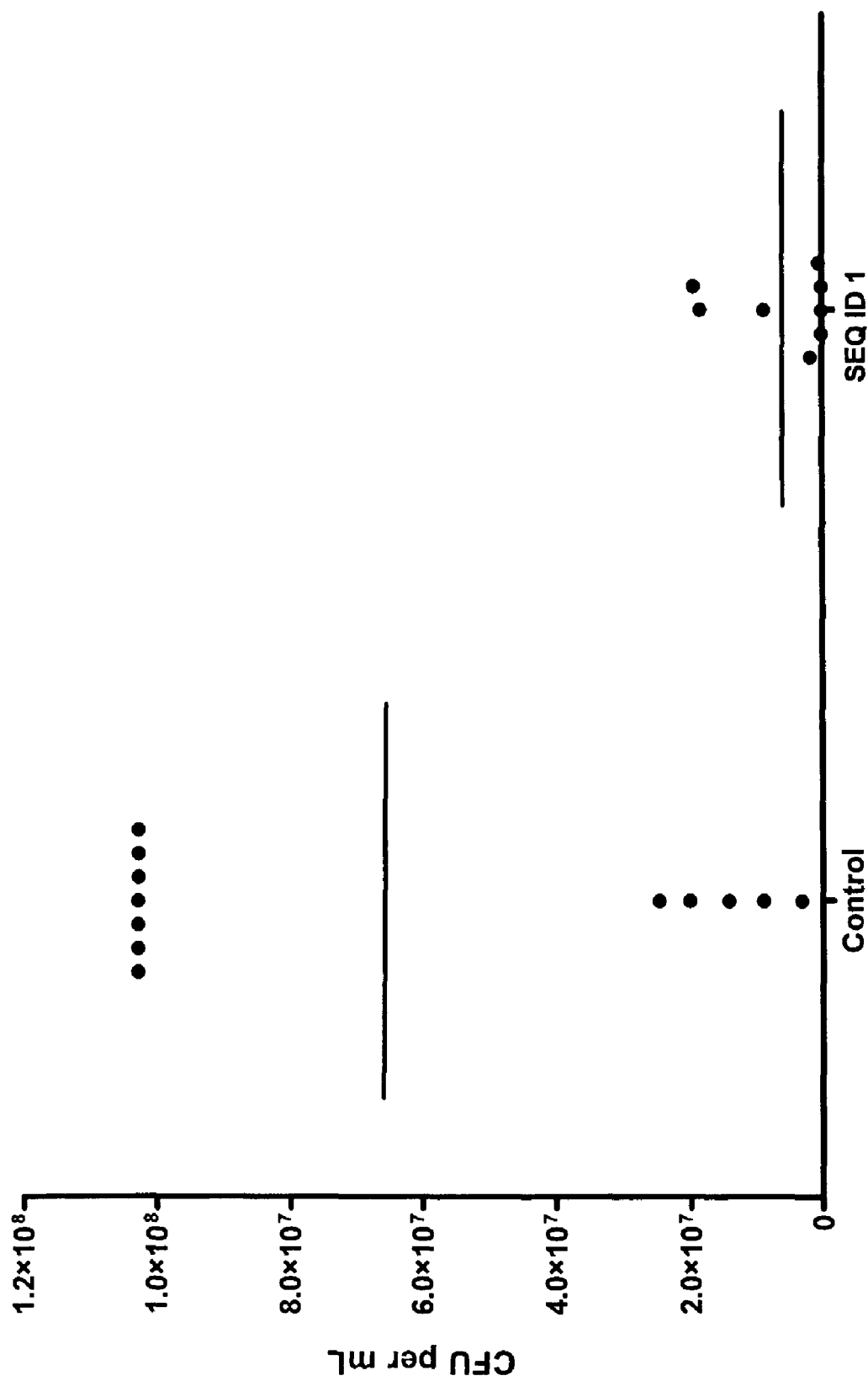
Figure 2C:
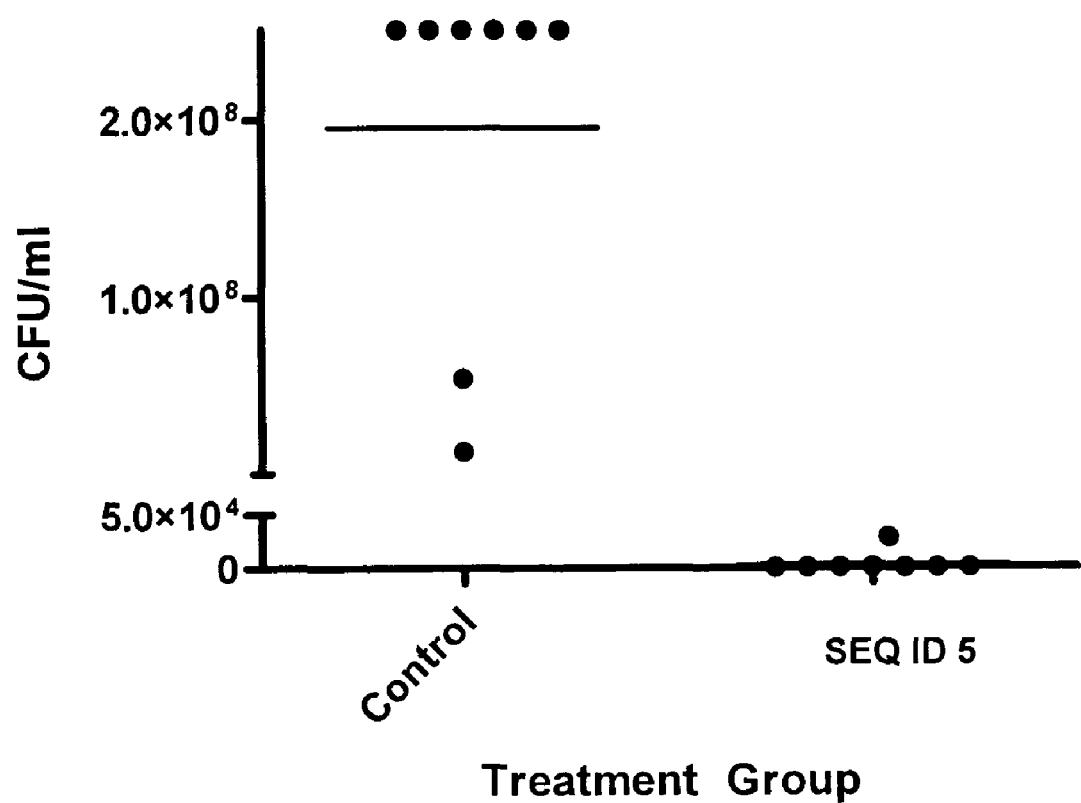
Figure 2D:
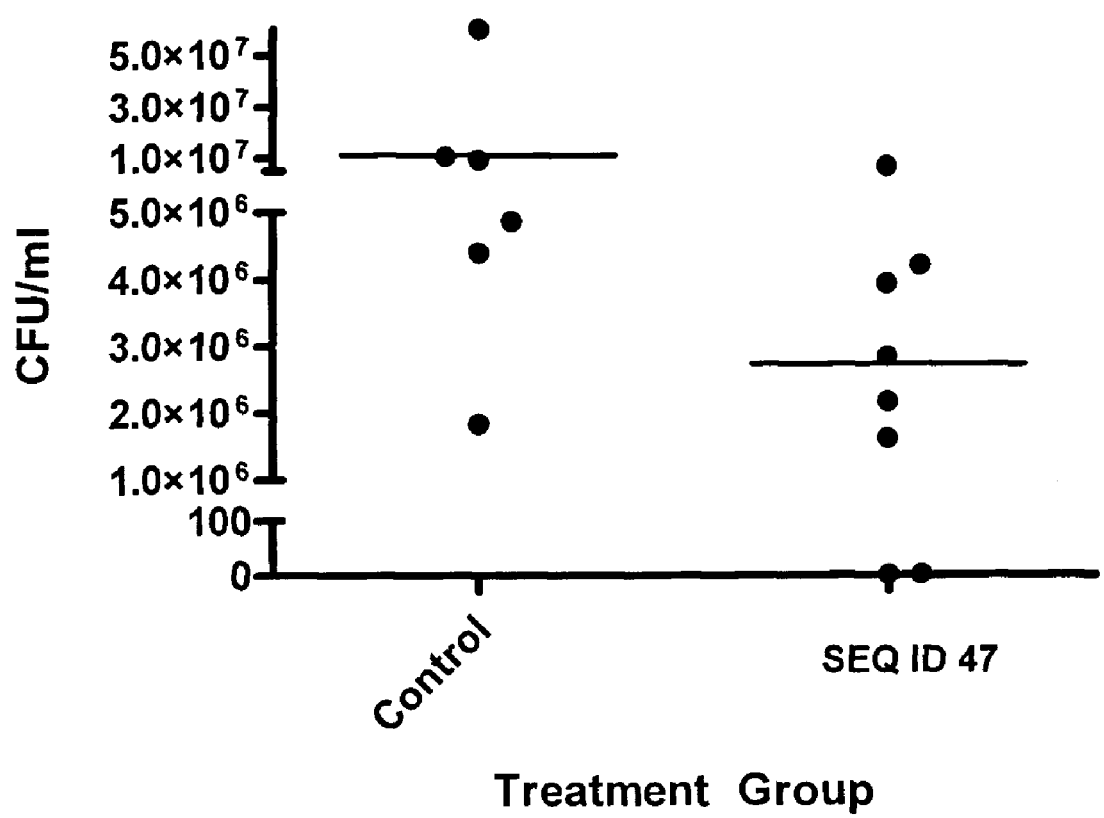
Figure 2E:
Figure 2F:
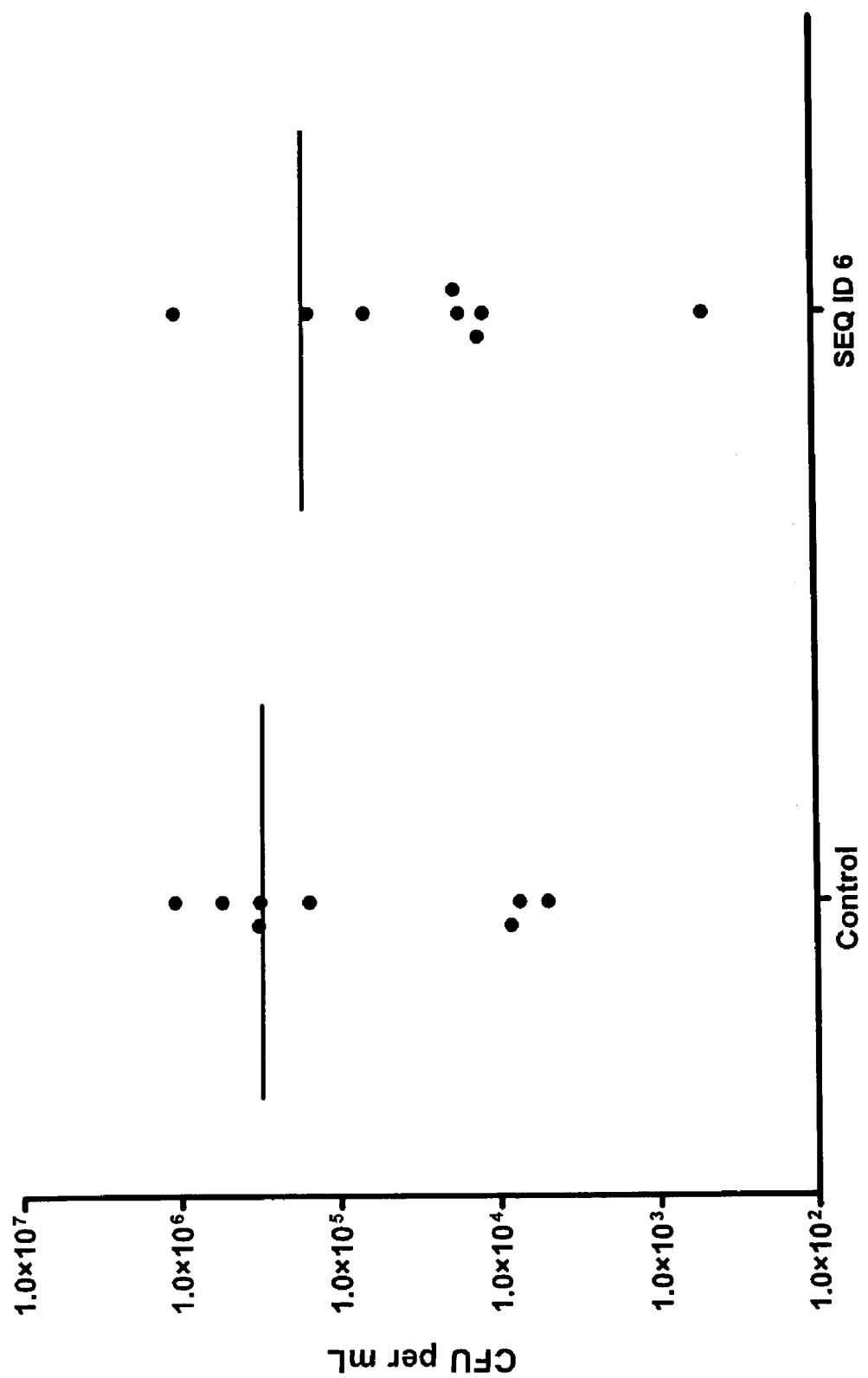
Figure 2G:
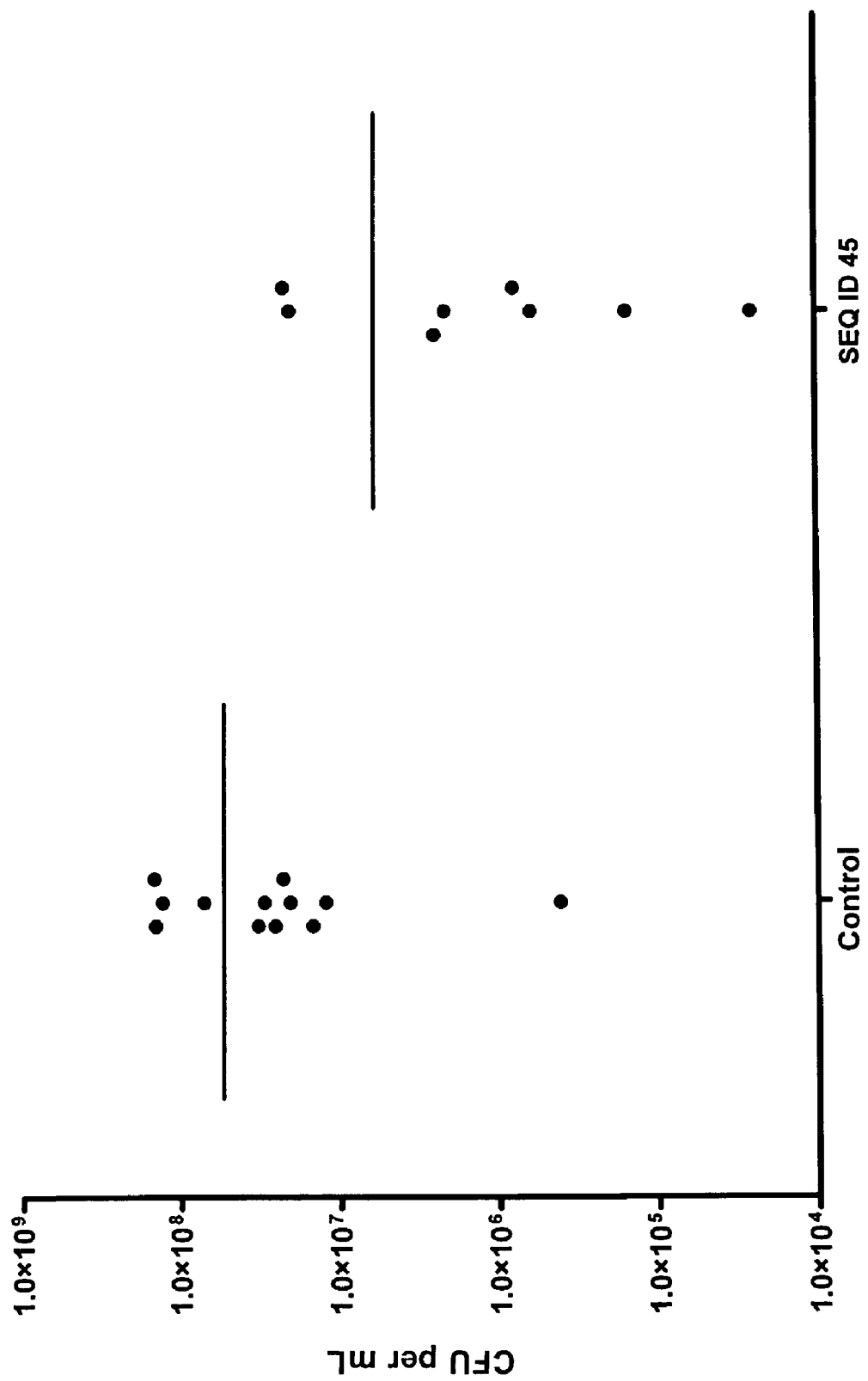

Mice were infected with *S. aureus* 25923 via intraperitoneal (IP) injection. Four hours later, the peptide of SEQ ID NOs: 1, 4, 5, 6, 45, and 47 were administered at 12 mg/kg and 24 mg/kg for SEQ ID NO:1 (FIGS. 2A and 2B), 9.6 mg/kg for SEQ ID NO: 5 (FIG. 2C), 13 mg/kg for SEQ ID NO: 47 (FIG. 2D), 12 mg/kg for SEQ ID NO: 4 (FIG. 2E), 9 mg/kg for SEQ ID NO:6 (FIG. 2F), and 13 mg/kg for SEQ ID NO:45 (FIG. 2G), via IP injection. Twenty-four hours post-infection, surviving animals were sacrificed, and intraperitoneal lavage fluid was plated to determine residual bacterial counts (# colony forming units per ml (CFU/ml)) in the presence and absence of peptide treatment.

Dead animals were assigned the highest bacterial count of any animal in the study. The peptide of SEQ ID NOs: 1, 4, 5, 6, 45, and 47 clearly demonstrated protection, as compared with the control as shown in FIG. 2 A-G.

Example 4

Prophylactic In Vivo Protection

Figure 3A:
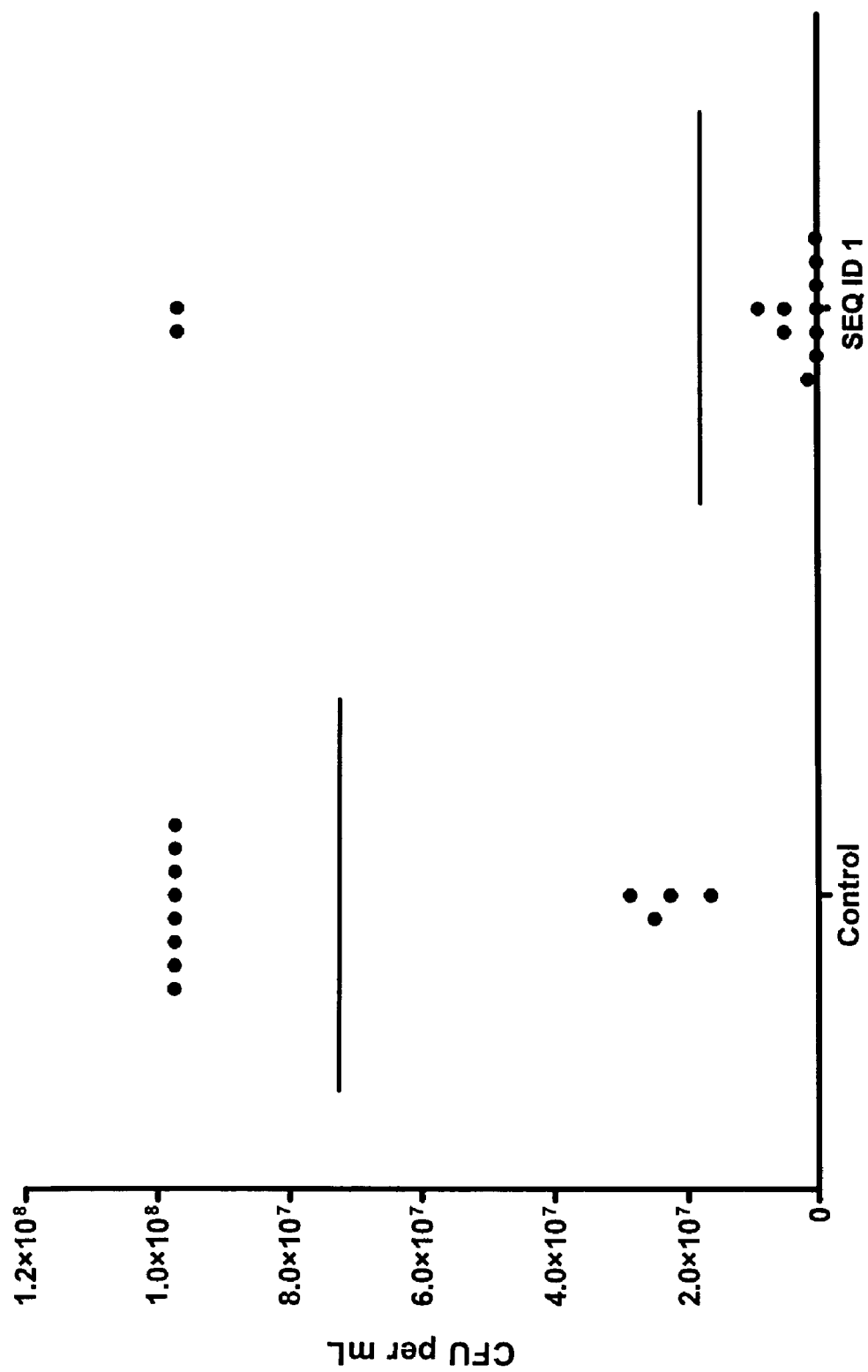
FIGS. 3 A and B depicts the results of the experiment described in Example 4. The graph shows colony-forming units per ml (CFU/ml) on the Y-axis, and treatment group (control=no peptide; SEQ ID NOs: 1 and 5=treatment with a peptide having the respective amino acid sequence) on the X-axis. The bacterial count of individual mice is shown.
Figure 3B:
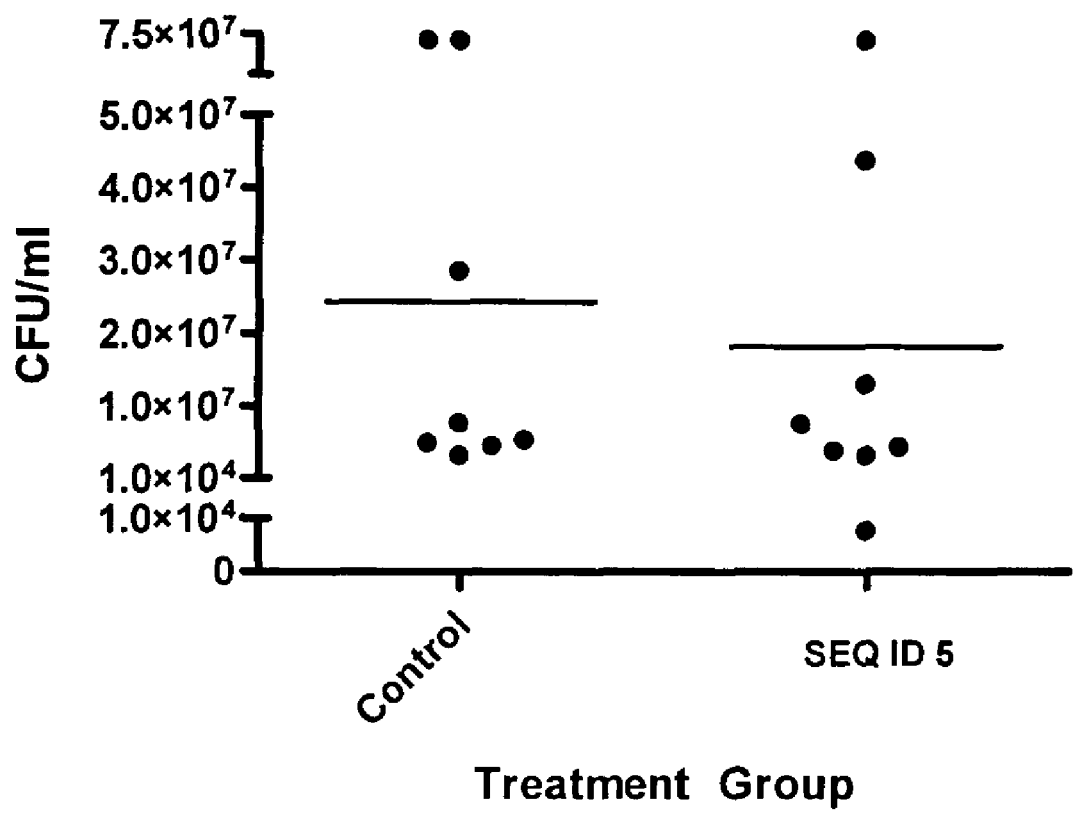

Twenty-four hours prior to infection, peptide was administered at 12 mg/kg (SEQ ID NO: 1, FIG. 3A) and 11.5 mg/kg (SEQ ID NO: 5, FIG. 3B), via IP injection. Mice were then infected with *S. aureus* 25923 via IP injection. Twenty-four hours post-infection, surviving animals were sacrificed and intraperitoneal lavage fluid was plated to determine residual bacterial counts (# colony forming units per ml (CFU/ml)) in the presence and absence of peptide treatment.

Dead animals were assigned the highest bacterial count of any animal in the study. The peptides of SEQ ID NOs: 1 and 5 clearly demonstrated protection ((0 mouse dead (peptide treatment) vs. 2 mice dead (control)). Please see FIGS. 3 A and B.

Figure 1B:
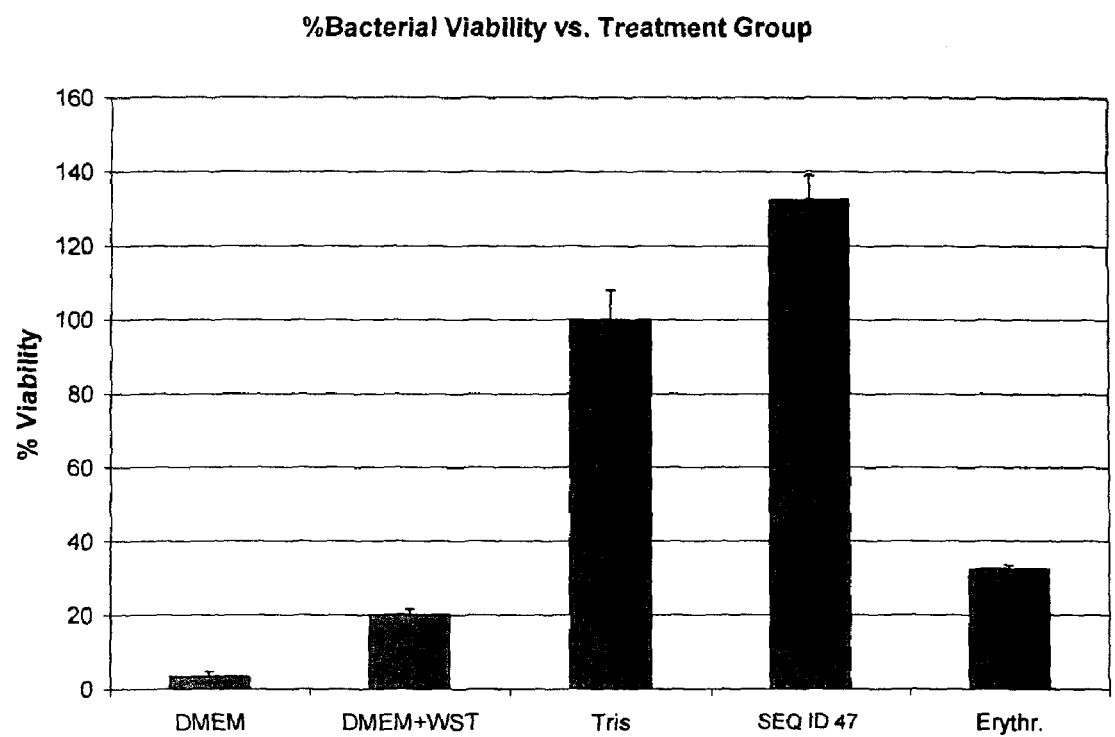

Discussed below are results obtained by the inventors in connection with the experiments of Examples 1-4:

The inventors have shown that a peptide having the amino acid sequence of those shown in TABLE 1 or as described herein as part of the invention can enhance innate immunity. Specifically, the peptides of SEQ ID NOs:1, 4, 5, 6, 45, and 47 had the ability to prevent and protect against infection, as demonstrated in in vivo models (FIG. 2 and Example 3; FIG. 3 and Example 4) However, the peptide of SEQ ID NOs:5 and 47 lacked antimicrobial activity, as shown in Example 1 and FIG. 1. Accordingly, modulation of innate immunity, via the peptide of SEQ ID NOs:5 and/or 47, indicate that these peptides can be used as a therapeutic for the treatment of infectious disease.

Example 5

Plasma DPPIV Activity Assay with Mouse Blood

Mouse blood was obtained by cardiac puncture from ICR mice and collected in heparinized blood collection tubes. Blood from several mice was pooled and aliquoted into 300 µL aliquots. The peptide was dissolved in acetate buffered saline, pH 5.5, to a concentration of 9 mM. Of this stock solution 30 µL were added to 300 µL of blood and mixed by resuspension (concentration in blood 0.82 mM). For the control, 30 µL of blank acetate buffered saline was added to 300 µL of blood. Each peptide group was prepared in triplicate, whereas the control was prepared in six replicates. The samples were incubated at 37° C. in closed microtubes for two hours. After incubation the plasma was isolated from the samples by centrifugation at 4000 rcf. The plasma was transferred to a 96-well assay plate for the DPPIV assay. The assay was started by adding 5 µL of the DPPIV substrate gly-pro-p-nitroanilide (16 mM in de-ionized water) to 95 µL of plasma (concentration in plasma 0.8 mM) and the increase in UV absorbance (405 nm) was monitored over a 20 min time period. The rate of the production of p-nitroaniline by enzymatic cleavage of gly-pro-p-nitroanilide was taken as the activity of DPPIV (Durinx C et al., (2001) "Reference values for plasma dipeptidyl-peptidase IV activity and their association with other laboratory parameters". Clin Chem Lab Med. 39(2):155-9.)

The results can be seen in TABLE 1. The effect of the peptides on the activity of DPPIV was observed. Results are presented as normalized, averaged % activity relative to saline control (set to 100%). Anything less than 100% activity represents a reduction in DPPIV activity.

In one aspect of the invention, a reduction by of DPPIV activity by about, or in one embodiment, at least, 25% (i.e. to about 75%) was deemed to be active. A person skilled in the art would appreciate that the desired level of activity may vary depending on the use of the peptides.

Discussion

The type II transmembrane serine protease dipeptidyl peptidase IV (DPPIV), also known as CD26 or adenosine deaminase binding protein, is a major regulator of various physiological processes including immune functions. CD26/DPPIV is a 110-kD cell surface glycoprotein that is mainly expressed on mature thymocytes, activated T-cells, B-cells, NK-cells, macrophages, and epithelial cells. It has at least two functions, a signal transduction function and a proteolytic function (Morimoto C, Schlossman S F. The structure and function of CD26 in.—. The T-cell immune response. Immunol. Review. 1998, 161: 55-70). One of its cellular roles involves modulation of chemokine activity by cleaving dipeptides from the chemokine N-terminus. The modulation of the $NH_2$ termini of chemokines is of great importance not only for binding to their receptors and the following reactions but also for altering the receptor specificity of the processed chemokine. Furthermore, it was demonstrated that soluble rCD26 enhances transendothelial migration of T cells whereas it reduces the migratory response of monocytes [Oravecz, T. et. al., (1997) Regulation of the receptor specificity and formation of the chemokine RANTES (regulated on activation, normal T cell expressed and secreted) by dipeptidyl peptidase IV (CD26)-mediated cleavage. J. Exp. Med. 186:1865-1872; Iwata, S., et. al., (1999) CD26/dipeptidyl peptidase IV differentially regulates the chemotaxis of T cells and monocytes toward RANTES: possible mechanism for the switch from innate to acquired immune response. Int. Immunol. 11:417-426). These results indicate that CD26/DPPIV differentially regulate the chemotactic response of T cells and monocytes and is involved in the switch from innate to acquired immune response. As such, a reduction in activity of DPPIV would then have the opposite effect, promoting an innate immune response and macrophage migratory responses. It has also been reported that pharmacological inhibition of DPPIV enzyme activity could reduce the progression of arthritis in an experimental rat model of RA (Tanaka S et al., Anti-arthritic effects of the novel dipeptidyl peptidase IV inhibitors TMC-2A and TSL-225. Immunopharmacology 1998, 40:21-26; Tanaka S, et al.: Suppression of arthritis by the inhibitors of dipeptidyl peptidase IV. Int J Immunopharmacol 1997, 19:15-24), suggesting that decreases in DPPIV-activity may alleviate inflammation under some circumstances. Together the anti-inflammatory role and its modulation of chemokine activity make DPPIV a good molecule for screening novel compounds for these activities.

CD26/DPPIV is involved in the pathology of a variety of diseases, such as AIDS and HIV disease progression (Blazquez et al. 1992; Vanham et al. 1993; Schols et al. 1998 Oravecz et al. 1995), Graves' disease (Eguchi et al. 1989; Nishikawa et al. 1995), and cancer (Stecca et al. 1997) and diabetes (Hinke et al. 2000; Marguet et al. 2000).

Further, CD26 as an indicator of T-cell activation has been shown to fluctuate in parallel with several autoimmune diseases such as rheumatoid arthritis (Nakao et al., 1989) and autoimmune thyroiditis (Eguchi et al., 1989). CD26 has been described as a marker that correlates well with the level of activity of these diseases. It has furthermore been studied as an indicator of disease progression in chronic progressive multiple sclerosis (Constantinescu et al., 1995).

The peptides of the present invention have demonstrated that they can reduce the activity of DPPIV. As such, they can be used in the treatment of certain immunological conditions, such as DPPIV-related or associated conditions, and may, in one aspect modulate innate immunity and inflammation, such as inflammation leading to sepsis.

While the foregoing invention has been described in some detail for purposes of clarity and understanding, it will be appreciated by one skilled in the art, from a reading of the disclosure, that various changes in form and detail can be made without departing from the true scope of the invention in the appended claims.

TABLE 1 all C-terminal amidated unless otherwise indicated****

| SEQ ID | Description | 1 | 2 | 3 | 4 | 5 | 6 | 7 | 8 | 9 | 10 | 11 | 12 | 13 | 14 | 15 | Length | Net charge | % DPPIV Activity (Saline)** |
|---|---|---|---|---|---|---|---|---|---|---|---|---|---|---|---|---|---|---|---|
| 1 |  |  |  |  | + | K | S | R | I | V | P |  |  |  |  |  | 6 | 3 | 74 |
| 2 |  |  |  | Ac | K | S | R | I | V | P |  |  |  |  |  |  | 6 | 2 | 92 |
| 3 |  |  |  |  | + | S | R | I | V | P | A |  |  |  |  |  | 6 | 2 | 54 |
| 4 |  |  |  |  | + | S | R | I | V | P |  |  |  |  |  |  | 5 | 2 | 62 |
| 5 |  |  |  |  |  | + | R | I | V | P | A |  |  |  |  |  | 5 | 2 | 68 |
| 6 |  |  |  |  |  | + | K | I | V | P | A |  |  |  |  |  | 5 | 2 | 62 |
| 7 |  |  |  |  |  | + | R | I | V | P | A* |  |  |  |  |  | 5 | 2 | 60 |
| 8 |  |  |  |  |  | + | R |  | V | P | A |  |  |  |  |  | 4 | 2 | 56 |
| 9 |  |  |  |  |  | + | R | I |  | P | A |  |  |  |  |  | 4 | 2 | 54 |
| 10 |  |  |  |  |  | + | R | I | V | P | A | OH |  |  |  |  | 5 | 1 | 51 |
| 11 |  |  |  |  |  | + | R | A | V | P | A |  |  |  |  |  | 5 | 2 | 41 |
| 12 |  |  |  |  | + | R | R | I | V | P | A |  |  |  |  |  | 6 | 3 | 56 |
| 13 |  |  |  |  |  | + | R | K | V | P | A |  |  |  |  |  | 5 | 3 | 49 |
| 14 |  |  |  |  |  | + | R | I | V | P | K |  |  |  |  |  | 5 | 3 | 67 |
| 15 |  |  |  |  |  | + | R | P | V | P | A |  |  |  |  |  | 5 | 2 | 20 |
| 16 |  |  |  |  |  | + | R | I | P | P | A |  |  |  |  |  | 5 | 2 | 71 |
| 17 |  |  |  |  |  | + | R | I | V | P | P |  |  |  |  |  | 5 | 2 | 81 |
| 18 |  |  |  |  |  | + | R | I | V | P | G | G | A |  |  |  | 7 | 2 | 67 |
| 19 |  |  |  |  | + | G | G | I | V | P | A |  |  |  |  |  | 6 | 1 | 67 |
| 20 |  |  |  |  |  | + | G | I | V | P | A |  |  |  |  |  | 5 | 1 | 72 |
| 21 |  |  |  |  |  | + | R | G | V | P | A |  |  |  |  |  | 5 | 2 | 64 |
| 22 |  |  |  |  |  | + | R | I | V | P | G |  |  |  |  |  | 5 | 2 | 68 |
| 23 |  |  |  |  |  | + | R | I | V | P | S |  |  |  |  |  | 5 | 2 | 69 |
| 24 |  |  |  |  |  | + | R | I | V | P | L |  |  |  |  |  | 5 | 2 | 72 |
| 25 |  |  |  |  |  | + | R | H | V | P | A |  |  |  |  |  | 5 | 2? | 40 |
| 26 |  |  |  |  |  |  | + | R | I | P | V | A |  |  |  |  | 5 | 2 | −11 |
| 27 |  |  |  |  |  | + | R | V | I | P | A |  |  |  |  |  | 5 | 2 | 69 |
| 28 |  |  |  |  |  | + | R | I | I | P | A |  |  |  |  |  | 5 | 2 | 19 |
| 29 |  |  |  |  |  |  | + | A | V | P | I | R |  |  |  |  | 5 | 2 | −11 |
| 30 |  |  |  |  |  |  | + | A | P | V | I | R |  |  |  |  | 5 | 2 | 33 |
| 31 |  |  |  |  |  |  | -R | I | V | P | A- |  |  |  |  |  | 5 | 1 |  |
| 32 |  |  |  |  |  | -C | R | I | V | P | A | C- |  |  |  |  | 7 | 1 | 27 |
| 33 |  |  |  |  |  | + | R | Ix | V | P | A |  |  |  |  |  | 5 | 2 | 70 |
| 34 |  |  |  |  |  | + | R | I | V | P | Ax |  |  |  |  |  | 5 | 2 | 75 |
| 35 |  |  |  |  |  | + | R | I | V | P | F |  |  |  |  |  | 5 | 2 | 74 |
| 36 |  |  |  |  |  | + | Cit | I | V | P | A |  |  |  |  |  | 5 | 1 |  |
| 37 |  |  |  |  |  | + | R | L | V | P | A |  |  |  |  |  | 5 | 2 | 39 |
| 38 |  |  |  |  |  | + | H | I | V | P | A |  |  |  |  |  | 5 | 1? | 51 |
| 39 |  |  |  |  |  | + | I | R | R | V | P | A |  |  |  |  | 6 | 3 | 46 |
| 40 |  |  |  |  |  | + | A | R | V | P | A |  |  |  |  |  | 5 | 2 | 66 |
| 41 |  |  |  |  |  | + | I | R | V | P | A |  |  |  |  |  | 5 | 2 | 60 |
| 42 |  |  |  |  |  | + | O | I | V | P | A |  |  |  |  |  | 5 | 2 | 48 |
| 43 |  |  |  |  |  | + | S | I | V | P | A |  |  |  |  |  | 5 | 1 | 73 |
| 44 |  |  |  |  | + | V | S | I | I | K | P | A | R | V | P | S | L | L | 13 | 3 | 73 |
| 45 |  |  |  |  |  | + | K | P | A | R | V | P | S |  |  |  | 7 | 3 | 32 |
| 46 |  |  |  |  |  | + | R |  | V | P | S | L | L |  |  |  | 6 | 2 | 69 |
| 47 |  |  |  |  |  | + | K | P | R | A | V | P |  |  |  |  | 6 | 3 | 50 |
| 48 |  |  |  |  |  | + | P | A | R | V | P |  |  |  |  |  | 5 | 2 | 63 |
| 49 |  |  |  |  |  |  | + | I | R | V | P |  |  |  |  |  | 4 | 2 | 64 |

TABLE 1-continued all C-terminal amidated unless otherwise indicated****

| SEQ ID | Description | 1 | 2 | 3 | 4 | 5 | 6 | 7 | 8 | 9 | 10 | 11 | 12 | 13 | 14 | 15 | Length | Net charge | % DPPIV Activity (Saline)** |
|---|---|---|---|---|---|---|---|---|---|---|---|---|---|---|---|---|---|---|---|
| 50 | | | | | | + | R | | V | P | S | | | | | | 8 | 2 | 65 |
| 51 | | | | | | + | R | | V | P | | | | | | | 3 | 2 | 73 |
| 52 | | | | | | | | + | P | S | V | P | G | S | | | 6 | 1 | 71 |
| 53 | | | | | + | G | L | K | H | P | S | | | | | | 6 | 2? | 69 |
| 54 | | | | | | + | R | I | V | P | A | I | P | V | S | L | L | 11 | 2 | −2 |
| 55 | See Note 1 | | | | | | | X$_1$ | X$_2$ | P | | | | | | | 3 | | |
| 56 | See Note 2 | | | | | | X$_1$ | X$_2$ | X$_3$ | P | | | | | | | 4 | | |
| 57 | See Note 3 | | | | | a | X$_1$ | X$_2$ | X$_3$ | P | | | | | | | 5 | | |
| 58 | See Note 4 | | | | | | X$_1$ | X$_2$ | X$_3$ | P | b | | | | | | 5 | | |
| 59 | See Note 5 | | | | a$_1$ | a$_2$ | X$_1$ | X$_2$ | X$_3$ | P | | | | | | | 6 | | |
| 60 | See Note 6 | | | | | a | X$_1$ | X$_2$ | X$_3$ | P | b | | | | | | 6 | | |

**% DPPIV Activity (Saline), where control is 100% activity (saline or vehicle alone without the peptide). About 75% or less activity relative to saline control is desirable.
****OH indicates the free acid form of the peptide. Ac indicates acetylated. O indicated Ornithine, Cit indicated Citrulline, x indicates NMe backbone (versus amide backbone).

Note 1 of Table 1:
X$_1$ is selected from the group consisting of K, H, R, S, T, O, Cit, Hci, Dab, Dpr or glycine based compounds with basic functional groups on the N-terminal (e.g., NLys), hSer, Val (betaOH) X$_2$ is selected from the group consisting of V, I, K, P, and H including an isolated peptide of up to 10 amino acids comprising an amino acid sequence of SEQ ID NO: 55.

Note 2 of Table 1:
wherein X$_1$ is selected from the group consisting of K, H, R, S, T, O, Cit, Hci, Dab, Dpr, or glycine based compounds with basic functional groups subsituted on the N-terminal (e.g. NLys), hSer, Val (betaOH) and wherein X$_2$ is selected from the group consisting of A, I, L, V, K, P, G, H, R, S, O, Dab, Dpr, Cit, Hci, Abu, Hva, Nle, and wherein X$_2$ can be N-methylated, and wherein X$_3$ is selected from the group consisting of I, V, P, wherein in one embodiment, X$_3$ is not N-methylated. In one embodiment, the isolated peptide can be an amino acid sequence of up to 10 amino acids, but is not SEQ ID NO: 2 or 17.

Note 3 of Table 1:
wherein X$_1$, X$_2$ and X$_3$ are defined as SEQ ID NO: 56, and wherein "a" is selected from the group consisting of S, P, I, R, C, T, L, V, A, G, K, H R, O, C, M, and F or an isolated peptide up to 10 amino acids comprising said sequences.

Note 4 of Table 1:
wherein X$_1$X$_2$X$_3$P are as defined as SEQ ID NO: 56 and "b" is selected from the group consisting of A, A*, G, S, L, F, K, C, I, V, T, Y, R, H, O, and M, but in one embodiment not P. In one embodiment, the isolated peptide is a peptide of up to 10 amino acids comprising SEQ ID NO: 58 but not SEQ ID NO: 17.

Note 5 of Table 1:
wherein X$_1$, X$_2$ and X$_3$ are as defined in SEQ ID NO: 56 and "a$_1$" is selected from the group consisting of K, I, R,, H, O, L, V, A, and G and "a$_2$" is selected from the group consisting of S, P, R T, H, K, O, L, V, A, G, S, and I. In one embodiment, "a$_1$" is not acetylated, or where a$_1$ is K, K is not acetylated or not SEQ ID NO: 2. In one embodiment, the isolated peptide comprises up to 10 amino acids comprising SEQ ID NO: 59.

Note 6 of Table 1:
wherein X$_1$, X$_2$ and X$_3$ are as defined in SEQ ID NO: 56 and where "a" is selected from the group consisting of S, R, K, H, O, T, I, L, V, A, and G and wherein "b" is selected from the group consisting of A, V, I, L, G, K, H, R, O, S, T, and F or a peptide of up to 10 amino acids comprising SEQ ID NO: 60.

REFERENCES CITED

Blazquez M V, Madueno J A, Gonzalez R, Jurado R, Bachovchin W W, Pena J, Munoz E. Selective decrease of CD26 expression in T cells from HIV-1-infected individuals. *J. Immunol.* 1992 Nov. 1; 149(9):3073-7.

Vanham G, Kestens L, De Meester I, Vingerhoets J, Penne G, Vanhoof G, Scharpe S, Heyligen H, Bosmans E, Ceuppens J L, et al. Decreased expression of the memory marker CD26 on both CD4+ and CD8+ T lymphocytes of HIV-infected subjects. *J Acquir Immune Defic Syndr.* 1993 July; 6(7): 749-57.

Schols D, Proost P, Struyf S, Wuyts A, De Meester I, Scharpe S, Van Damme J, De Clercq E. CD26-processed RANTES (3-68), but not intact RANTES, has potent anti-HIV-1 activity. Antiviral Res. 1998 October; 39(3):175-87. *Erratum in: Antiviral Res* 1999 January; 40(3):189-90.

Oravecz T, Roderiquez G, Koffi J, Wang J, Ditto M, Bou-Habib D C, Lusso P, Norcross M A. CD26 expression correlates with entry, replication and cytopathicity of monocytotropic HIV-1 strains in a T-cell line. *Nat Med* 1995 September; 1(9):919-26 Comment in: *Nat. Med.* 1995 September; 1(9):881-2.

Nishikawa Y, Nakamura M, Fukumoto K, Matsumoto M, Matsuda T, Tanaka Y, Yoshihara H. [Adenosine deaminase isoenzymes in patients with Graves' disease] *Rinsho Byori.* 1995 October,43(10):1057-60. [Article in Japanese]

Eguchi K, Ueki Y, Shimomura C, Otsubo T, Nakao H, Migita K, Kawakami A, Matsunaga M, Tezuka H, Ishikawa N, et al. Increment in the Ta1+ cells in the peripheral blood and thyroid tissue of patients with Graves' disease. *J Immunol* 1989 Jun. 15; 142(12):4233-40.

Stecca B A, Nardo B, Chieco P, Mazziotti A, Bolondi L, Cavallari A. Aberrant dipeptidyl peptidase IV (DPP IV/CD26) expression in human hepatocellular carcinoma. *J Hepatol.* 1997 August; 27(2):337-45.

Hinke S A, Pospisilik J A, Demuth H U, Mannhart S, Kuhn-Wache K, Hoffmann T, Nishimura E, Pederson R A, McIntosh C H. Dipeptidyl peptidase IV (DPIV/CD26) degradation of glucagon. Characterization of glucagon degradation products and DPIV-resistant analogs. *J Biol. Chem.* 2000 Feb. 11; 275(6):3827-34.

Marguet D, Baggio L, Kobayashi T, Bernard A M, Pierres M, Nielsen P F, Ribel U, Watanabe T, Drucker D J, Wagtmann N. Enhanced insulin secretion and improved glucose tolerance in mice lacking CD26. *Proc Natl Acad Sci USA.* 2000 Jun. 6; 97(12):6874-9.

Nakao H, Eguchi K, Kawakami A, Migita K, Otsubo T, Ueki Y, Shimomura C, Tezuka H, Matsunaga M, Maeda K, et al. Increment of Ta1 positive cells in peripheral blood from patients with rheumatoid arthritis. *J Rheumatol.* 1989 July; 16(7):904-10.

Constantinescu C S, Kamoun M, Dotti M, Farber R E, Galetta S L, Rostami A. A longitudinal study of the T cell activation marker CD26 in chronic progressive multiple sclerosis. *J Neurol Sci.* 1995 June; 130(2):178-82.

What is claimed is:

1. An isolated peptide consisting of the amino acid sequence of RIVPA SEQ ID NO: 5, or a pharmaceutical salt, ester or amide thereof.

2. A pharmaceutical composition comprising a peptide consisting of the amino acid sequence of RIVPA SEQ ID NO: 5, or pharmaceutical salt, ester or amide thereof and a pharmaceutically-acceptable carrier, diluent, or excipient.

3. The pharmaceutical composition according to claim 2, wherein the pharmaceutical carrier, diluent, or excipient is one or more selected from the group consisting of carboxymethyl cellulose, crystalline cellulose, glycerin, gum arabic, lactose, magnesium stearate, methyl cellulose, powders, saline, sodium alginate, sucrose, starch, talc, and water.

4. The pharmaceutical composition according to claim 3, wherein the pharmaceutical carrier is saline.

* * * * *

UNITED STATES PATENT AND TRADEMARK OFFICE
CERTIFICATE OF CORRECTION

| | | Page 1 of 1 |
|---|---|---|
| PATENT NO. | : 8,124,721 B2 | |
| APPLICATION NO. | : 12/083086 | |
| DATED | : February 28, 2012 | |
| INVENTOR(S) | : Oreola Donini | |

It is certified that error appears in the above-identified patent and that said Letters Patent is hereby corrected as shown below:

Col. 57, Claim 2, line 6, add a space between "sequence" and "of".

Col. 57, Claim 2, line 7, replace "or pharmaceutical salt" with -- or a pharmaceutical salt --.

Signed and Sealed this
Third Day of July, 2012

David J. Kappos
*Director of the United States Patent and Trademark Office*

SEQUENCE LISTING

<160> NUMBER OF SEQ ID NOS: 60

<210> SEQ ID NO 1
<211> LENGTH: 6
<212> TYPE: PRT
<213> ORGANISM: Artificial
<220> FEATURE:
<223> OTHER INFORMATION: IMMUNOLOGICAL PEPTIDE

<400> SEQUENCE: 1

Lys Ser Arg Ile Val Pro
1               5

<210> SEQ ID NO 2
<211> LENGTH: 6
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is equal to Acetylated K

<400> SEQUENCE: 2

Xaa Ser Arg Ile Val Pro
1               5

<210> SEQ ID NO 3
<211> LENGTH: 6
<212> TYPE: PRT
<213> ORGANISM: Artificial
<220> FEATURE:
<223> OTHER INFORMATION: IMMUNOLOGICAL PEPTIDE

<400> SEQUENCE: 3

Ser Arg Ile Val Pro Ala
1               5

<210> SEQ ID NO 4
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 4

Ser Arg Ile Val Pro
1               5

<210> SEQ ID NO 5
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 5

Arg Ile Val Pro Ala
1               5

<210> SEQ ID NO 6
<211> LENGTH: 5
<212> TYPE: PRT
<213> ORGANISM: Artificial
<220> FEATURE:
<223> OTHER INFORMATION: IMMUNOLOGICAL PEPTIDE -continued

```
<400> SEQUENCE: 6

Lys Ile Val Pro Ala
1               5

<210> SEQ ID NO 7
<211> LENGTH: 5
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (5)..(5)
<223> OTHER INFORMATION: Xaa is equal to D-Amino Acid of Ala

<400> SEQUENCE: 7

Arg Ile Val Pro Xaa
1               5

<210> SEQ ID NO 8
<211> LENGTH: 4
<212> TYPE: PRT
<213> ORGANISM: Artificial
<220> FEATURE:
<223> OTHER INFORMATION: IMMUNOLOGICAL PEPTIDE

<400> SEQUENCE: 8

Arg Val Pro Ala
1

<210> SEQ ID NO 9
<211> LENGTH: 4
<212> TYPE: PRT
<213> ORGANISM: Artificial
<220> FEATURE:
<223> OTHER INFORMATION: IMMUNOLOGICAL PEPTIDE

<400> SEQUENCE: 9

Arg Ile Pro Ala
1

<210> SEQ ID NO 10
<211> LENGTH: 5
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (5)..(5)
<223> OTHER INFORMATION: Xaa is equal to Ala-OH

<400> SEQUENCE: 10

Arg Ile Val Pro Xaa
1               5

<210> SEQ ID NO 11
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 11

Arg Ala Val Pro Ala
1               5
```

```
<210> SEQ ID NO 12
<211> LENGTH: 6
<212> TYPE: PRT
<213> ORGANISM: Artificial
<220> FEATURE:
<223> OTHER INFORMATION: IMMUNOLOGICAL PEPTIDE

<400> SEQUENCE: 12

Arg Arg Ile Val Pro Ala
1               5

<210> SEQ ID NO 13
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 13

Arg Lys Val Pro Ala
1               5

<210> SEQ ID NO 14
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 14

Arg Ile Val Pro Lys
1               5

<210> SEQ ID NO 15
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 15

Arg Pro Val Pro Ala
1               5

<210> SEQ ID NO 16
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 16

Arg Ile Pro Pro Ala
1               5

<210> SEQ ID NO 17
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 17

Arg Ile Val Pro Pro
1               5

<210> SEQ ID NO 18
<211> LENGTH: 7
```

```
<212> TYPE: PRT
<213> ORGANISM: Artificial
<220> FEATURE:
<223> OTHER INFORMATION: IMMUNOLOGICAL PEPTIDE

<400> SEQUENCE: 18

Arg Ile Val Pro Gly Gly Ala
1               5

<210> SEQ ID NO 19
<211> LENGTH: 6
<212> TYPE: PRT
<213> ORGANISM: Artificial
<220> FEATURE:
<223> OTHER INFORMATION: IMMUNOLOGICAL PEPTIDE

<400> SEQUENCE: 19

Gly Gly Ile Val Pro Ala
1               5

<210> SEQ ID NO 20
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 20

Gly Ile Val Pro Ala
1               5

<210> SEQ ID NO 21
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 21

Arg Gly Val Pro Ala
1               5

<210> SEQ ID NO 22
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 22

Arg Ile Val Pro Gly
1               5

<210> SEQ ID NO 23
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 23

Arg Ile Val Pro Ser
1               5

<210> SEQ ID NO 24
<211> LENGTH: 5
<212> TYPE: PRT
<213> ORGANISM: Artificial
```

```
<220> FEATURE:
<223> OTHER INFORMATION: IMMUNOLOGICAL PEPTIDE

<400> SEQUENCE: 24

Arg Ile Val Pro Leu
1               5

<210> SEQ ID NO 25
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 25

Arg His Val Pro Ala
1               5

<210> SEQ ID NO 26
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 26

Arg Ile Pro Val Ala
1               5

<210> SEQ ID NO 27
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 27

Arg Val Ile Pro Ala
1               5

<210> SEQ ID NO 28
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 28

Arg Ile Ile Pro Ala
1               5

<210> SEQ ID NO 29
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 29

Ala Val Pro Ile Arg
1               5

<210> SEQ ID NO 30
<211> LENGTH: 5
<212> TYPE: PRT
<213> ORGANISM: Artificial
<220> FEATURE:
<223> OTHER INFORMATION: IMMUNOLOGICAL PEPTIDE
```

```
<400> SEQUENCE: 30

Ala Pro Val Ile Arg
1               5

<210> SEQ ID NO 31
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 31

Arg Ile Val Pro Ala
1               5

<210> SEQ ID NO 32
<211> LENGTH: 7
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(7)
<223> OTHER INFORMATION: cyclic peptide

<400> SEQUENCE: 32

Cys Arg Ile Val Pro Ala Cys
1               5

<210> SEQ ID NO 33
<211> LENGTH: 5
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (2)..(2)
<223> OTHER INFORMATION: Xaa is equal to I with an NMe backbone

<400> SEQUENCE: 33

Arg Xaa Val Pro Ala
1               5

<210> SEQ ID NO 34
<211> LENGTH: 5
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (5)..(5)
<223> OTHER INFORMATION: Xaa is equal to A with an N-methylated backbone

<400> SEQUENCE: 34

Arg Ile Val Pro Xaa
1               5

<210> SEQ ID NO 35
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 35
```

```
Arg Ile Val Pro Phe
1               5

<210> SEQ ID NO 36
<211> LENGTH: 5
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is equal to Citrulline

<400> SEQUENCE: 36

Xaa Ile Val Pro Ala
1               5

<210> SEQ ID NO 37
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 37

Arg Leu Val Pro Ala
1               5

<210> SEQ ID NO 38
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 38

His Ile Val Pro Ala
1               5

<210> SEQ ID NO 39
<211> LENGTH: 6
<212> TYPE: PRT
<213> ORGANISM: Artificial
<220> FEATURE:
<223> OTHER INFORMATION: IMMUNOLOGICAL PEPTIDE

<400> SEQUENCE: 39

Ile Arg Arg Val Pro Ala
1               5

<210> SEQ ID NO 40
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 40

Ala Arg Val Pro Ala
1               5

<210> SEQ ID NO 41
<211> LENGTH: 5
<212> TYPE: PRT
<213> ORGANISM: Artificial
<220> FEATURE:
<223> OTHER INFORMATION: IMMUNOLOGICAL PEPTIDE
```

```
<400> SEQUENCE: 41

Ile Arg Val Pro Ala
1               5

<210> SEQ ID NO 42
<211> LENGTH: 5
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is equal to Ornithine

<400> SEQUENCE: 42

Xaa Ile Val Pro Ala
1               5

<210> SEQ ID NO 43
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 43

Ser Ile Val Pro Ala
1               5

<210> SEQ ID NO 44
<211> LENGTH: 13
<212> TYPE: PRT
<213> ORGANISM: Artificial
<220> FEATURE:
<223> OTHER INFORMATION: IMMUNOLOGICAL PEPTIDE

<400> SEQUENCE: 44

Val Ser Ile Ile Lys Pro Ala Arg Val Pro Ser Leu Leu
1               5                   10

<210> SEQ ID NO 45
<211> LENGTH: 7
<212> TYPE: PRT
<213> ORGANISM: Artificial
<220> FEATURE:
<223> OTHER INFORMATION: IMMUNOLOGICAL PEPTIDE

<400> SEQUENCE: 45

Lys Pro Ala Arg Val Pro Ser
1               5

<210> SEQ ID NO 46
<211> LENGTH: 6
<212> TYPE: PRT
<213> ORGANISM: Artificial
<220> FEATURE:
<223> OTHER INFORMATION: IMMUNOLOGICAL PEPTIDE

<400> SEQUENCE: 46

Arg Val Pro Ser Leu Leu
1               5

<210> SEQ ID NO 47
<211> LENGTH: 6
<212> TYPE: PRT
<213> ORGANISM: Artificial
<220> FEATURE:
```

<223> OTHER INFORMATION: IMMUNOLOGICAL PEPTIDE

<400> SEQUENCE: 47

Lys Pro Arg Ala Val Pro
1               5

<210> SEQ ID NO 48
<211> LENGTH: 5
<212> TYPE: PRT
<213> ORGANISM: Artificial
<220> FEATURE:
<223> OTHER INFORMATION: IMMUNOLOGICAL PEPTIDE

<400> SEQUENCE: 48

Pro Ala Arg Val Pro
1               5

<210> SEQ ID NO 49
<211> LENGTH: 4
<212> TYPE: PRT
<213> ORGANISM: Artificial
<220> FEATURE:
<223> OTHER INFORMATION: IMMUNOLOGICAL PEPTIDE

<400> SEQUENCE: 49

Ile Arg Val Pro
1

<210> SEQ ID NO 50
<211> LENGTH: 4
<212> TYPE: PRT
<213> ORGANISM: Artificial
<220> FEATURE:
<223> OTHER INFORMATION: IMMUNOLOGICAL PEPTIDE

<400> SEQUENCE: 50

Arg Val Pro Ser
1

<210> SEQ ID NO 51
<211> LENGTH: 3
<212> TYPE: PRT
<213> ORGANISM: Artificial
<220> FEATURE:
<223> OTHER INFORMATION: IMMUNOLOGICAL PEPTIDE

<400> SEQUENCE: 51

Arg Val Pro
1

<210> SEQ ID NO 52
<211> LENGTH: 6
<212> TYPE: PRT
<213> ORGANISM: Artificial
<220> FEATURE:
<223> OTHER INFORMATION: IMMUNOLOGICAL PEPTIDE

<400> SEQUENCE: 52

Pro Ser Val Pro Gly Ser
1               5

<210> SEQ ID NO 53
<211> LENGTH: 6
<212> TYPE: PRT
<213> ORGANISM: Artificial
<220> FEATURE:
<223> OTHER INFORMATION: IMMUNOLOGICAL PEPTIDE

```
<400> SEQUENCE: 53

Gly Leu Lys His Pro Ser
1               5

<210> SEQ ID NO 54
<211> LENGTH: 11
<212> TYPE: PRT
<213> ORGANISM: Artificial
<220> FEATURE:
<223> OTHER INFORMATION: IMMUNOLOGICAL PEPTIDE

<400> SEQUENCE: 54

Arg Ile Val Pro Ala Ile Pro Val Ser Leu Leu
1               5                   10

<210> SEQ ID NO 55
<211> LENGTH: 3
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer,
      Val(betaOH)
<220> FEATURE:
<221> NAME/KEY: misc_feature
<222> LOCATION: (2)..(2)
<223> OTHER INFORMATION: Xaa is selected from the group consisting of V,
      I, K, P, and H

<400> SEQUENCE: 55

Xaa Xaa Pro
1

<210> SEQ ID NO 56
<211> LENGTH: 4
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer,
      Val(betaOH)
<220> FEATURE:
<221> NAME/KEY: misc_feature
<222> LOCATION: (2)..(2)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: misc_feature
<222> LOCATION: (3)..(3)
<223> OTHER INFORMATION: Xaa is selected from the group consisting of I,
      V, P

<400> SEQUENCE: 56

Xaa Xaa Xaa Pro
1

<210> SEQ ID NO 57
<211> LENGTH: 5
<212> TYPE: PRT
<213> ORGANISM: Artificial
<220> FEATURE:
```

-continued

```
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is selected from the group consisting of S,
      P , I,  R, C, T, L, V, A, G, K, H, R, O, C, M, and F
<220> FEATURE:
<221> NAME/KEY: misc_feature
<222> LOCATION: (2)..(2)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer,
      Val(betaOH)
<220> FEATURE:
<221> NAME/KEY: misc_feature
<222> LOCATION: (3)..(3)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: misc_feature
<222> LOCATION: (4)..(4)
<223> OTHER INFORMATION: Xaa is selected from the group consisting of I,
      V, P

<400> SEQUENCE: 57

Xaa Xaa Xaa Xaa Pro
1               5

<210> SEQ ID NO 58
<211> LENGTH: 5
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer,
      Val(betaOH)
<220> FEATURE:
<221> NAME/KEY: misc_feature
<222> LOCATION: (2)..(2)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: misc_feature
<222> LOCATION: (3)..(3)
<223> OTHER INFORMATION: Xaa is selected from the group consisting of I,
      V, P
<220> FEATURE:
<221> NAME/KEY: misc_feature
<222> LOCATION: (5)..(5)
<223> OTHER INFORMATION: Xaa is selected from the group consisting of A,
      A*,G, S, L, F, K, C, I, V, T, Y, R, H, O, and M, wherein A*
      denotes D amino acid of A

<400> SEQUENCE: 58

Xaa Xaa Xaa Pro Xaa
1               5

<210> SEQ ID NO 59
<211> LENGTH: 6
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is selected from the group consisting of K,
      I, R, H, O, L, V, A, and G
<220> FEATURE:
```

```
<221> NAME/KEY: misc_feature
<222> LOCATION: (2)..(2)
<223> OTHER INFORMATION: Xaa is selected from the group consisting of S,
      P, R, T, H, K, O, L, V, A, G, S, I
<220> FEATURE:
<221> NAME/KEY: misc_feature
<222> LOCATION: (3)..(3)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer,
      Val(betaOH)
<220> FEATURE:
<221> NAME/KEY: misc_feature
<222> LOCATION: (4)..(4)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: misc_feature
<222> LOCATION: (5)..(5)
<223> OTHER INFORMATION: Xaa is selected from the group consisting of I,
      V, P

<400> SEQUENCE: 59

Xaa Xaa Xaa Xaa Xaa Pro
1               5

<210> SEQ ID NO 60
<211> LENGTH: 6
<212> TYPE: PRT
<213> ORGANISM: Artificial
<220> FEATURE:
<223> OTHER INFORMATION: IMMUNOLOGICAL PEPTIDE
<220> FEATURE:
<221> NAME/KEY: misc_feature
<222> LOCATION: (1)..(1)
<223> OTHER INFORMATION: Xaa is selected from the group consisting of S,
      R, K, H, O, T, I, L, V, A, and G
<220> FEATURE:
<221> NAME/KEY: misc_feature
<222> LOCATION: (2)..(2)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer,
      Val(betaOH)
<220> FEATURE:
<221> NAME/KEY: misc_feature
<222> LOCATION: (3)..(3)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: misc_feature
<222> LOCATION: (4)..(4)
<223> OTHER INFORMATION: Xaa is selected from the group consisting of I,
      V, P
<220> FEATURE:
<221> NAME/KEY: misc_feature
<222> LOCATION: (6)..(6)
<223> OTHER INFORMATION: Xaa is selected from the group consisting of A,
      V, I, L, G, K, H, R, O, S, T, and F

<400> SEQUENCE: 60

Xaa Xaa Xaa Xaa Pro Xaa
1               5
```